(12) United States Patent
Watanasiri et al.

(10) Patent No.: US 11,101,020 B2
(45) Date of Patent: Aug. 24, 2021

(54) MOLECULAR CHARACTERIZATION METHOD AND SYSTEM

(71) Applicant: Aspen Technology, Inc., Bedford, MA (US)

(72) Inventors: Suphat Watanasiri, Bedford, MA (US); Shu Wang, Bedford, MA (US); Lili Yu, Shanghai (CN); Christopher Quan, Haverhill, MA (US)

(73) Assignee: ASPEN TECHNOLOGY, INC., Bedford, MA (US)

( * ) Notice: Subject to any disclaimer, the term of this patent is extended or adjusted under 35 U.S.C. 154(b) by 520 days.

(21) Appl. No.: 15/961,310

(22) Filed: Apr. 24, 2018

(65) Prior Publication Data
US 2018/0307803 A1    Oct. 25, 2018

Related U.S. Application Data
(60) Provisional application No. 62/489,087, filed on Apr. 24, 2017.

(51) Int. Cl.
*G16C 20/30* (2019.01)
*G16C 20/20* (2019.01)

(52) U.S. Cl.
CPC ............. *G16C 20/30* (2019.02); *G16C 20/20* (2019.02)

(58) Field of Classification Search
CPC ................................. G16C 20/30; G16C 20/20
USPC .......................................................... 702/27
See application file for complete search history.

(56) References Cited

U.S. PATENT DOCUMENTS

| | | | |
|---|---|---|---|
| 5,223,714 A | 6/1993 | Maggard | |
| 5,600,134 A | 2/1997 | Ashe et al. | |
| 5,699,269 A | 12/1997 | Ashe et al. | |
| 5,808,180 A | 9/1998 | Roussis et al. | |
| 6,662,116 B2 | 12/2003 | Brown | |
| 7,598,487 B2 | 10/2009 | Qian et al. | |
| 8,546,146 B2 | 10/2013 | Butler | |
| 8,916,722 B2 | 12/2014 | Yaghi et al. | |

(Continued)

FOREIGN PATENT DOCUMENTS

| | | |
|---|---|---|
| EP | 2 584 381 A1 | 4/2013 |
| EP | 2788754 A1 | 10/2014 |

(Continued)

OTHER PUBLICATIONS

Fernandez-Lima, et al., "Petroleum Crude Oil Characterization by IMS-MS and FTICR MS," Anal. Chem, vol. 81, No. 24, pp. 9941-9947, Dec. 15, 2009.

(Continued)

*Primary Examiner* — Michael P Nghiem
*Assistant Examiner* — Dacthang P Ngo
(74) *Attorney, Agent, or Firm* — Hamilton, Brook, Smith & Reynolds, P.C.

(57) ABSTRACT

Computer-implemented methods of characterizing chemical composition of a sample containing crude oil or a petroleum fraction are presented. The methods can include, in a processor, receiving assay data of the sample, and particularly molecular-level data obtained using advanced analytical techniques, and processing this data in view of a model library of compounds, including reconciling compound compositions, to form a characterization of the chemical composition of the sample.

30 Claims, 41 Drawing Sheets

(56) References Cited

U.S. PATENT DOCUMENTS

| | | | |
|---|---|---|---|
| 8,975,084 | B2 | 3/2015 | Qian et al. |
| 9,418,828 | B2 | 8/2016 | Mennito et al. |
| 9,490,109 | B2 | 11/2016 | Qian et al. |
| 9,625,439 | B2 | 4/2017 | Saeger et al. |
| 9,934,367 | B2 | 4/2018 | Chen et al. |
| 10,393,723 | B2 | 8/2019 | Watanasiri et al. |
| 2003/0195708 | A1 | 10/2003 | Brown |
| 2007/0043546 | A1 | 2/2007 | Fontes et al. |
| 2007/0050154 | A1 | 3/2007 | Albahri |
| 2008/0248967 | A1 | 10/2008 | Butler et al. |
| 2009/0105966 | A1 | 4/2009 | Brown et al. |
| 2012/0153139 | A1 | 6/2012 | Qian et al. |
| 2013/0185044 | A1* | 7/2013 | Chen ................. G01N 33/2823 703/12 |
| 2013/0325362 | A1 | 12/2013 | Saeger et al. |
| 2014/0221711 | A1 | 8/2014 | Chitta |
| 2015/0106028 | A1 | 4/2015 | Koseoglu et al. |
| 2016/0140674 | A1 | 5/2016 | Mendoza et al. |
| 2016/0162664 | A1 | 6/2016 | Watanasiri et al. |
| 2019/0228843 | A1 | 7/2019 | Hou et al. |

FOREIGN PATENT DOCUMENTS

| | | |
|---|---|---|
| EP | 3289495 A | 11/2016 |
| JP | 10-185875 | 7/1998 |
| JP | H 11-508363 A | 7/1999 |
| JP | 3493028 B2 | 11/2003 |
| JP | 2005-512051 A | 4/2005 |
| JP | 2008-513562 A | 5/2008 |
| JP | 2009-525461 A | 7/2009 |
| JP | 2014-500506 A | 1/2014 |
| JP | 2014-503816 A | 2/2014 |
| JP | 2015-507747 | 3/2015 |
| JP | 2016-503884 A | 2/2016 |
| JP | 6240091 | 11/2017 |
| JP | 2020-165976 A | 10/2020 |
| JP | 2020-166779 A | 10/2020 |
| WO | 1997-01183 A1 | 1/1997 |
| WO | WO 1997/01096 A | 1/1997 |
| WO | 2003/093815 A1 | 11/2003 |
| WO | 2004/081680 A1 | 9/2004 |
| WO | WO 2006/030218 A1 | 3/2006 |
| WO | 2007-061935 A2 | 5/2007 |
| WO | 2012-082504 A2 | 6/2012 |
| WO | 2012-083095 A2 | 6/2012 |
| WO | 2012/142467 A2 | 10/2012 |
| WO | WO 2003/048759 A1 | 6/2013 |
| WO | WO 2013/106755 | 7/2013 |
| WO | 2014-099312 A1 | 6/2014 |
| WO | WO 2016/178763 | 11/2016 |
| WO | 2018/200521 A2 | 11/2018 |

OTHER PUBLICATIONS

Hsu, et al., "Petroleomics: advanced molecular probe for petroleum heavy ends," Journal of Mass Spectrometry, vol. 46, No. 4, pp. 337-343, Mar. 24, 2011.

Qian et al., "Resolution and Identification of Elemental Compositions for More than 3000 Crude Acids in Heavy Petroleum by Negative-Ion Microelectrospray High-Field Fourier Transform Ion Cyclotron Resonance Mass Spectrometry," Energy and Fuels, vol. 15, No. 5, pp. 1505-1511, 2001.

Tanaka, et al., "Analysis of the Molecular Weight Distribution of Petroleum Asphaltenes Using Laser Desorption-Mass Spectrometry," Energy & Fuels, vol. 18, No. 5, pp. 1405-1413, 2004.

International Search Report and the Written Opinion of the International Searching Authority, International Application No. PCT/US2018/029135; entitled "Molecular Characterization Method and System", filed Apr. 24, 2018, dated Nov. 20, 2018.

Riazi, M. R.; "Characterization and Properties of Petroleum Fractions;" Chapter 1—Introduction, pp. 1-29; American Society for Testing and Materials (2005).

Albahri, T. A., "Molecularly Explicit Characterization Model (MECM) for Light Petroleum Fractions," *Ind. Eng. Chem. Res.*, 44:9286-9298 (2005).

An, A. and Hao, X., "Generalized Predictive Control for a Precise Crude Oil Blending Process," *Proceedings of the IEEE, International Conference on Automation and Logistics* (2008).

Eckert, E. and Vaněk, T., "New Approach to the Characterization of Petroleum Mixtures Used in the Modelling of Separation Processes," *Computers & Chem. Eng.*, 30:343-356 (2005).

Gross, J. and Sadowski, G., "Perturbed-Chain SAFT: An Equation of State Based on a Perturbation Theory for Chain Molecules," *Ind. Eng. Chem. Res.* 40: 1244-1260 (2001).

Gross, J. et al., "Modeling Copolymer Systems Using the Perturbed-Chain SAFT Equation of State," *Ind. Eng. Chem. Res.* 42: 1266-1274 (2003).

Hudebine, D., et al., "Statistical Reconstruction of Gas Oil Cuts," *Oil & Gas Science Technology*, 66(3): 461-477 (2009).

International Preliminary Report on Patentability for Int'l Application No. PCT/US2013/021294 entitled: Method of Characterizing Chemical Composition of Crude Oil for Petroleum Refining Processing; dated Jul. 24, 2014.

International Preliminary Report on Patentability for Int'l Application No. PCT/US2016/025929 entitled, "Method to Represent Metal Content in Crude Oils, Reactor Feedstocks, and Reactor Products," dated Nov. 7, 2017.

International Search Report and the Written Opinion of the International Searching Authority, or the Declaration for PCT/US2013/021294, dated Mar. 28, 2013.

Jaffe, S. B., et al., "Extension of Structure-Oriented Lumping to Vacuum Residua," *Ind. Eng. Chem. Res.*, 44:9840-9852 (2005).

Klein, et al., "Molecular Modeling in Heavy Hydrocarbon Conversions," *Taylor & Francis*, (2006).

McKenna, A., et al. "Unprecedented Ultrahigh Resolution FT-ICR Mass Spectrometry and Parts-Per-Billion Mass Accuracy Enable Direct Characterization of Nickel and Vanadyl Porphyrins in Petroleum from Natural Seeps," *Energy Fuels*, 28: 2454-2464 (2014).

NIST ThermoData Engine (NIST Standard Reference Database 103b, http://trc.nist.gov/tde.html) (several pages from website, printed Feb. 17, 2016).

Notification of Transmittal of the International Search Report and the Written Opinion of the International Searching Authority, or the Declaration, PCT/US2016/025929, "Method to Represent Metal Content in Crude Oils, Reactor Feedstocks, and Reactor Products", dated Jul. 6, 2016.

Oil & Gas Journal Databook, 2006 Edition, PennWell Corporation, Tulsa, Oklahoma, 2006 (cover pages).

Peng, "Molecular modelling of petroleum processes," dissertation, University of Manchester, 1999.

Poling, Bruce, E., et al., "Viscosity", *The Properties of Gases and Liquids McGraw-Hill*, $5^{th}$ Ed., Chapter 9, pp. 9.77-9.90 (2001).

Pyl, S. P., et al., "Modeling the Composition of Crude Oil Fractions Using Constrained Homologous Series," *Ind. Eng. Chem. Res.* 50: 10850-10858 (2011).

Quann, R. J. and Jaffe, S. B., "Structured-Oriented Lumping: Describing the Chemistry of Complex Hydrocarbon Mixtures," *Ind. Eng. Chem. Res.*, 31: 2483-2497 (1992).

Riazi, M.R., "Characterization and Properties of Petroleum Fractions", *Petroleum Fractions*, ASTM International, Chapter 3, pp. 111-119 (2005).

Saine Aye, M. M. and Zhang, N., "A Novel Methodology in Transforming Bulk Properties of Refining Streams into Molecular Information," *Chem. Eng. Sci.*, 60: 6702-6717 (2005).

Sebor, G., et al., "Effect of the Type of Organometallic Iron and Copper Compounds on the Determination of Both Metals in Petroleum Samples by Flame Atomic-absorption Spectroscopy", *Analyst*, 107:1350-1355 (Nov. 1982).

Verstraete, J. J., et al., Molecular 1-16 Reconstruction of Heavy Petroleum Residue Fractions, *Chemical Engineering Science*, Oxford, GB, vol. 65, No. 1., pp. 304-312 (2010).

Watt, Murray, R., et al., "Crude Assay", *Practical Advances in Petroleum Processing*, vol. 1, Chapter 3, Chang S. Hsu & Paul R. Robinson, Eds., Springer, pp. 103-116, (2006).

(56) References Cited

OTHER PUBLICATIONS

Wu, Y. and Zhang, N., "Molecular Characterization of Gasoline and Diesel Streams," *Ind. Eng. Chem. Res.*, 49: 12773-12782 (2010).

Dixon, A.G. et al., "Packed tubular reactor modeling and cataylst design using computational fluid dynamics," Advances in Chemical Engineering, vol. 31, 307-389 (2006).

International Search Report and the Written Opinion of the International Searching Authority, International Application No. PCT/US2019/013954 entitled "Molecule-Based Equation Oriented Reactor Simulation System and Its Model Reduction," filed Jan. 17, 2019, dated Jun. 18, 2019.

Korre, S.C. et al., "Hydrocracking of polynuclear aromatic hydrocarbons. Development of rate laws through inhibition studies," Industrial & Engineering Chemistry Research, 36:6 (1997).

Salciccioli, M. et al., "A review of multiscale modeling of metal-catalyzed reactions: Mechanism development for complexity and emergent behavior," Chemical Engineering Science 66:19, 4319-4355 (2011).

Yossefi, D. et al., "Stimulation and implementation of laminar flow reactors for the study of combustion systems of ethane, methane and deborane," Fuel, IPC Science and Technology Press, 77:3, 173-181 (1998).

International Preliminary Report on Patentability, for Internationnal Application No. PCT/US2018/029135, entitled, "Molecular Characterization Method and System," dated Nov. 7, 2019, 8 pages.

International Preliminary Report on Patentability for International Application No. PCT/US2019/013954 entitled "Molecule-Based Equation Oriented Reactor Simulation System and Its Model Reduction," dated Jul. 30, 2020.

\* cited by examiner

FIG. 8

| | | PETROLEUM FRACTION BOILING POINT RANGE (°C) | | | | | | | | | | | |
|---|---|---|---|---|---|---|---|---|---|---|---|---|---|
| DATA TYPE | MOLECULAR DETAIL | INITIAL-100 | 100-160 | 160-200 | 200-260 | 240-300 | 300-350 | 350-395 | 395-425 | 425-450 | 450-500 | 500-560 | >560 |
| GC-MS | EXACT | 1st | 1st | 1st | | | | | | | | | |
| GC-ToF | QUANTITATIVE | | | | 1st | 1st | 1st | | | | | | |
| APPI FT-ICR MS | QUALITATIVE | | | | | | | 1st | 1st | 1st | 1st | 1st | 1st |
| ESI+/- FT-ICR MS | QUALITATIVE | | | 2nd | 2nd | 2nd | 2nd | 1st | 1st | 1st | 1st | 1st | 1st |
| DENSITY | N/A (TRADITIONAL) | 2nd | 2nd | 2nd | 3rd | 3rd | 3rd | 2nd | 2nd | 2nd | 2nd | 2nd | 2nd |
| VISCOSITY | N/A (TRADITIONAL) | 2nd | 2nd | 2nd | 3rd | 3rd | 3rd | 2nd | 2nd | 2nd | 2nd | 2nd | |
| TAN | N/A (TRADITIONAL) | | | | 3rd | 3rd | 3rd | 2nd | 2nd | 2nd | 2nd | 2nd | 2nd |
| CCR | N/A (TRADITIONAL) | 2nd | 2nd | 3rd | 3rd | 3rd | 3rd | 2nd | 2nd | 2nd | 2nd | 2nd | 2nd |
| ELEMENTAL COMP (C,H,S,N) | N/A (TRADITIONAL) | 2nd | 2nd | 3rd | 3rd | 3rd | 3rd | 2nd | 2nd | 2nd | 2nd | 2nd | 2nd |

Table 1: Example Compound Classes
| Index | Compound Class | Class Type | Sample Compound |
|---|---|---|---|
| Hydrocarbon molecules | | | |
| 1 | Paraffin/P | HC | 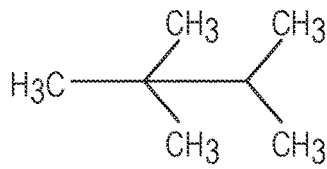 |
| 2 | Naphthene/N | HC | 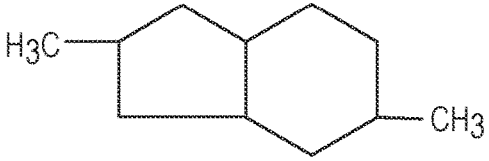 |
| 3 | Aromatic/A | HC | 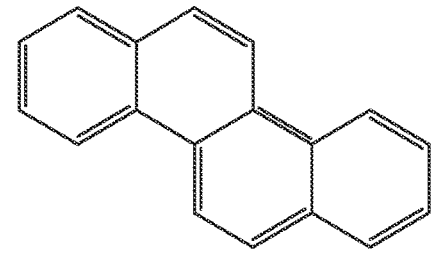 |
| 4 | Olefin/O | HC | 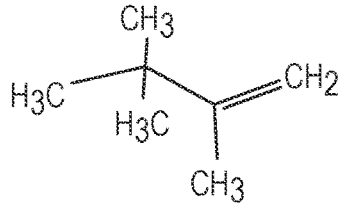 |
FIG. 19

Table 1: Example Compound Classes
| Sulfur molecules | | | |
|---|---|---|---|
| 5 | Mercaptan/M | S1 | 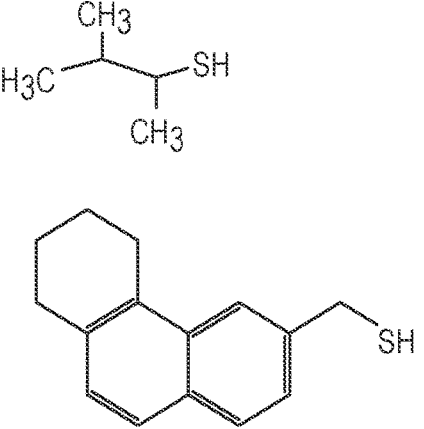 |
| 6 | Thiophene/sulfide/S1 | S1 | 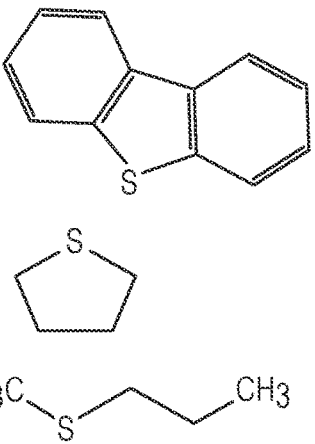 |
| 7 | Thiophene/sulfide/S2 | S2 | 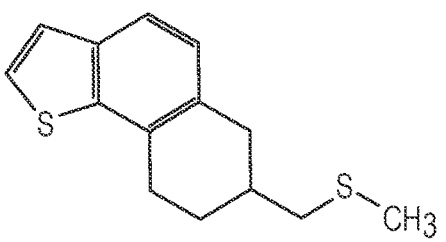 |
FIG. 19 (Continued)

Table 1: Example Compound Classes
| | | | |
|---|---|---|---|
| | | | 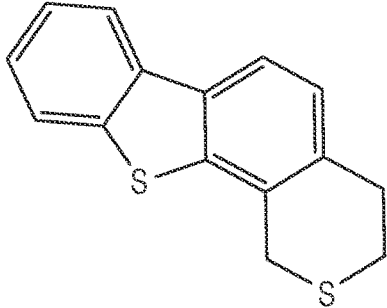 |
| 8 | Sulfoxide/S1OX | S1Ox | 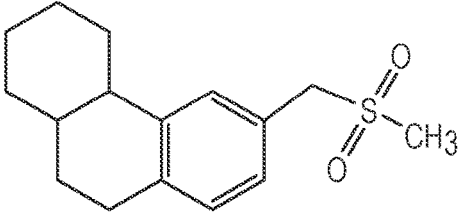 |
| 9 | Sulfur-oxygen/S1Ox | S1Ox | 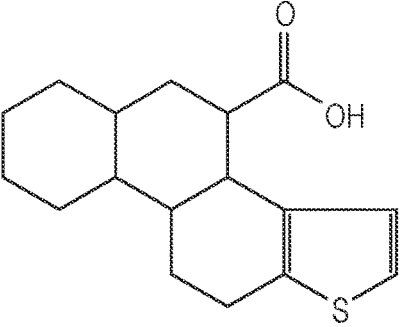 |
FIG. 19 (Continued)

Table 1: Example Compound Classes
| | | | |
|---|---|---|---|
| | | | 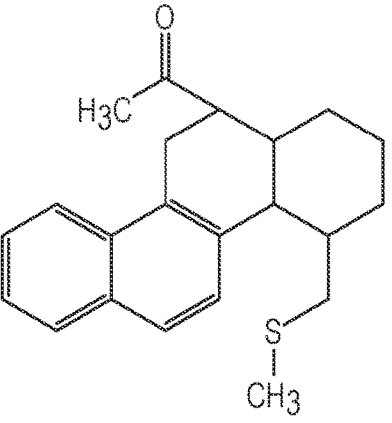 |
| Neutral nitrogen molecules | | | |
| 10 | Neutral nitrogen/N1 | N1 | 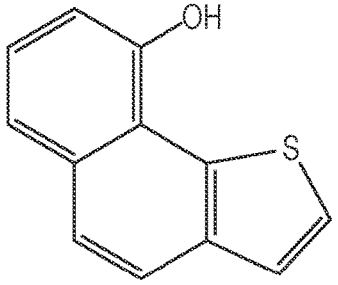 |
FIG. 19 (Continued)

Table 1: Example Compound Classes
| 11 | Neutral nitrogen/N2 | N2 | 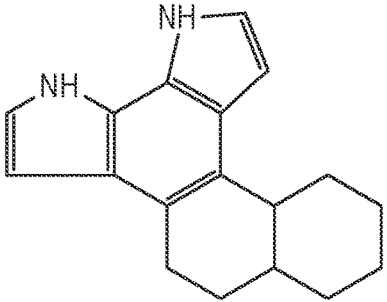 |
| --- | --- | --- | --- |
| 12 | Neutral nitrogen-sulfur/N1S1 | N1S1 | 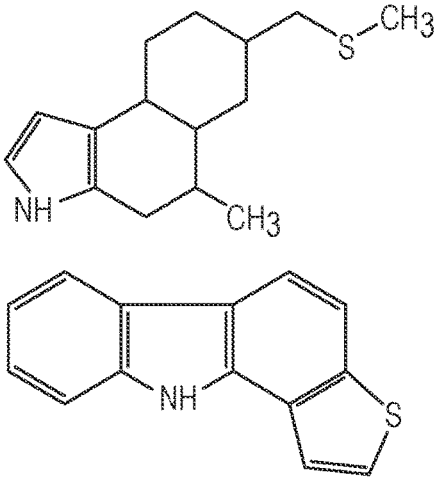 |
| 13 | Neutral nitrogen-oxygen/N1Ox | N1Ox | 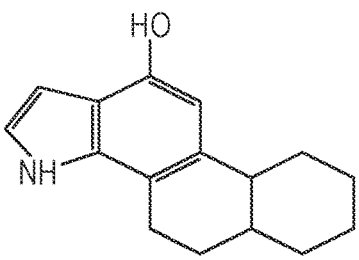 |
FIG. 19 (Continued)

Table 1: Example Compound Classes
| | | | |
|---|---|---|---|
| | | | 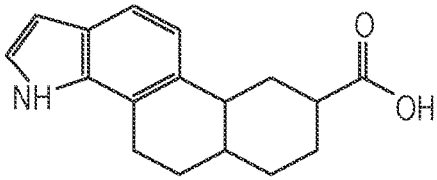 |
| Basic nitrogen molecules | | | |
| 14 | Basic nitrogen/N1 | N1 | 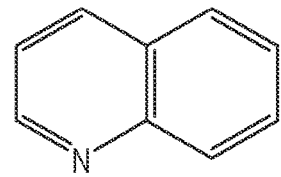 |
| 15 | Basic nitrogen/N2 | N2 | 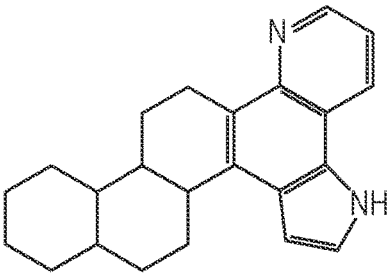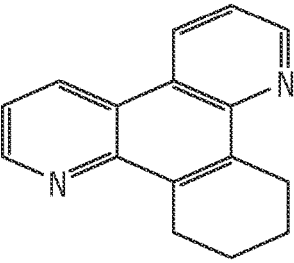 |
FIG. 19 (Continued)

Table 1: Example Compound Classes
| 16 | Basic nitrogen-sulfur/N1S1 | N1S1 | 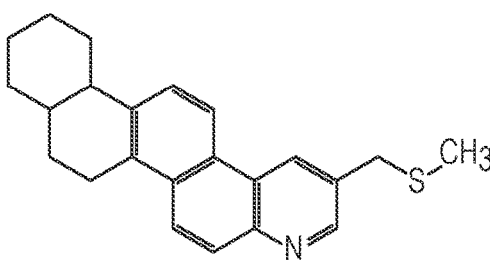 |
| --- | --- | --- | --- |
| 17 | Basic nitrogen-oxygen/N1Ox | N1Ox | 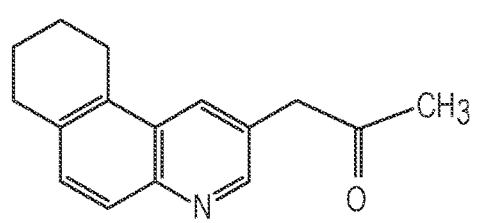 |
| Oxygen molecules | | | |
FIG. 19 (Continued)

Table 1: Example Compound Classes
| 18 | Phenol/PH | O1 | 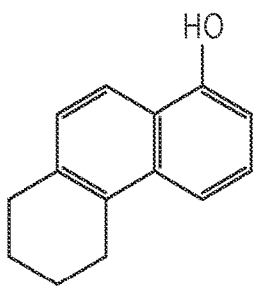 |
| --- | --- | --- | --- |
| 19 | Paraffinic acid/PA | O2 | 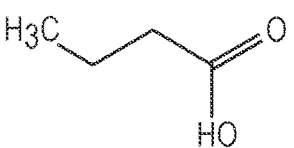 |
| 20 | Aromatic and Naphthenic acid/NA&AA | O2 | 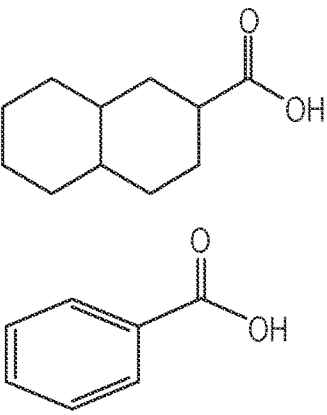 |
FIG. 19 (Continued)

Table 1: Example Compound Classes
| Porphyrin molecules | | | |
|---|---|---|---|
| 21 | Nickel Porphyrin/Ni | Ni | 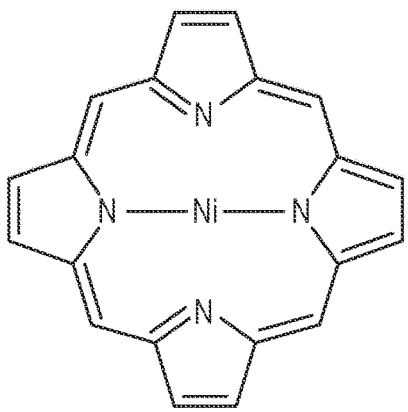 |
| 22 | Vanadium Porphyrin/VO | VO | 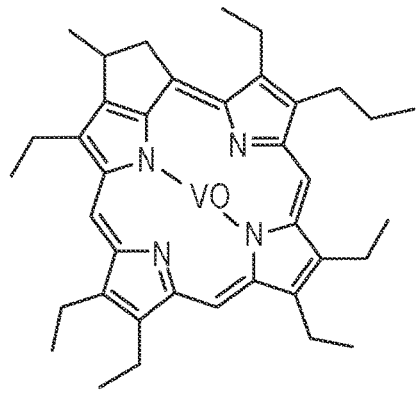 |
FIG. 19 (Continued)

Table 2: Example of molecules in the MC Library, their PC - SAFT functional groups, and the frequency of each functional group.
| Molecule | CH3 | CH | C(CH3)2 | CH2(N6) | ACH |
|---|---|---|---|---|---|
| 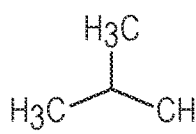 H3C—CH3 | 2 | 0 | 0 | 0 | 0 |
| 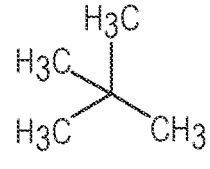 (isobutane) | 3 | 1 | 0 | 0 | 0 |
| 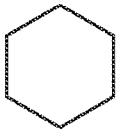 (neopentane) | 2 | 0 | 1 | 0 | 0 |
| (cyclohexane) | 0 | 0 | 0 | 6 | 0 |
| (benzene) | 0 | 0 | 0 | 0 | 6 |
FIG. 20

Table 3: PC-SAFT Functional Groups

| Hydrocarbon Segments | | | |
|---|---|---|---|
| Paraffin | Napthenes | Aromatics | Olefins |
| CH3 | CH2(N6) | ACH | CHCC2H6 |
| CH2CH2 | CH2(N5) | AC-CH2 | CH2CH |
| CH | CHCH-N6 | AC-CH3 | CH2C |
| C(CH3)2 | N5-CH2 | PACC | |
| CHCH-P | N5-CH3 | MAC | |
| CC(CH3)4 | N6-CH2 | ACO-N | |
| | N6-CH3 | CC-DIPHE | |

FIG. 21

Table 3: PC-SAFT Functional Groups

| Heteroatom Segments | | | |
|---|---|---|---|
| Sulfur | Oxygen | Nitrogen | Porphyrin |
| S–O | COOH | C3HN-N | PORPH |
| O–S–O | N6-COOH | C3HN-A | VO |
| S-P | AC-COOH | N | NI |
| SH | C–O | C4H5N | |
| SHCHCH3 | AC-OH | C4H4N | |
| SHCC2H6 | | C4H3N-N | |

FIG. 21 (Continued)

Table 3. PC-SAFT Functional Groups

| S-1 | | C4H3N-A | |
|---|---|---|---|
| S-N | | C4HN | |
| T-A(C2S) | | | |
| T-N(C2S) | | | |

FIG. 21 (Continued)

Table 4: Conceptual segment types and segment structures representing compound classes in Table 1.

| Compound Class | Segment Type | Segment Structure |
|---|---|---|
| Hydrocarbons molecules | | |
| Paraffins [HC] | Total carbon number | $-CH_2-$ |
| | One-branch methylene | |
| | Two-branch methylene | |
| Naphthenes [HC] | Total carbon number | $-CH_2-$ |
| | Naphthenic side ring | |
| | Mole fraction of 6CR | |
| Aromatics [HC] | Total carbon number | $-CH_2-$ |
| | Aromatic side ring | |
| | Naphthenic side ring | |
| Olefins [HC] | Total carbon number | $-CH_2-$ |
| | One-branch methylene | |
| | Two-branch methylene | |
| Sulfur molecules | | |
| Mercaptans [S1] | Total carbon number | $-CH_2-$ |
| | One-branch methylene | |
| | Two-branch methylene | |
| | Aromatic side ring | |
| | Naphthenic side ring | |
| Thiophene/Sulfide [S1] | Total carbon number | $-CH_2-$ |
| | Aromatic side ring | |
| | Naphthenic side ring | |
| Thiophene/Sulfide [S2] | Total carbon number | $-CH_2-$ |
| | Aromatic side ring | |
| | Naphthenic side ring | |
| | Mole fraction of Paraffinic Sulfide | |
| Sulfoxides [S1Ox] | Total carbon number | $-CH_2-$ |
| | Aromatic side ring | |
| | Naphthenic side ring | |
| | Mole fraction of SO2 | |

FIG. 22

Table 4: Conceptual segment types and segment structures representing compound classes in Table 1.

| Sulfur-Oxygen [S1Ox] | Total carbon number | $-CH_2-$ |
|---|---|---|
| | Aromatic side ring | ⌬ |
| | Naphthenic side ring | ⬡ |
| | Mole fraction of Phenol | |
| | Mole fraction of Thiophene | |
| Neutral Nitrogen molecules | | |
| Neutral Nitrogen [N1] | Total carbon number | $-CH_2-$ |
| | Aromatic side ring | ⌬ |
| | Naphthenic side ring | ⬡ |
| Neutral Nitrogen [N2] | Total carbon number | $-CH_2-$ |
| | Aromatic side ring | ⌬ |
| | Naphthenic side ring | ⬡ |
| Neutral Nitrogen-Sulfur [N1S1] | Total carbon number | $-CH_2-$ |
| | Aromatic side ring | ⌬ |
| | Naphthenic side ring | ⬡ |
| | Mole fraction of Paraffinic Sulfide | |
| Neutral Nitrogen-Oxygen [N1Ox] | Total carbon number | $-CH_2-$ |
| | Aromatic side ring | ⌬ |
| | Naphthenic side ring | ⬡ |
| | Mole fraction of NO2 | |
| Basic Nitrogen molecules | | |
| Basic Nitrogen [N1] | Total carbon number | $-CH_2-$ |
| | Aromatic side ring | ⌬ |
| | Naphthenic side ring | ⬡ |
| Basic Nitrogen [N2] | Total carbon number | $-CH_2-$ |
| | Aromatic side ring | ⌬ |
| | Naphthenic side ring | ⬡ |
| | Mole fraction of Neutral Nitrogen | |
| Basic Nitrogen-Sulfur [N1S1] | Total carbon number | $-CH_2-$ |
| | Aromatic side ring | ⌬ |
| | Naphthenic side ring | ⬡ |
| | Mole fraction of Basic Nitrogen Paraffinic Sulfide | |
| Basic Nitrogen-Oxygen [N1Ox] | Total carbon number | $-CH_2-$ |
| | Aromatic side ring | ⌬ |
| | Naphthenic side ring | ⬡ |

FIG. 22 (Continued)

Table 4: Conceptual segment types and segment structures representing compound classes in Table 1.

|  | Mole fraction of NO2 |  |
| --- | --- | --- |
| Oxygen molecules |  |  |
| Phenols [O1] | Total carbon number | -CH$_2$- |
|  | Aromatic side ring | ⬡ |
|  | Naphthenic side ring | ⬡ |
| Paraffinic acids [O2] | Total carbon number | -CH$_2$- |
| Aromatic acids [O2] | Total carbon number | -CH$_2$- |
|  | Aromatic side ring | ⬡ |
|  | Naphthenic side ring | ⬡ |
|  | Mole fraction of Aromatic Acid |  |
| Porphyrin molecules |  |  |
| Nickel porphyrins [Ni] | Total carbon number | -CH$_2$- |
|  | Aromatic side ring | ⬡ |
|  | Naphthenic side ring | ⬡ |
| Vanadium porphyrins [VO] | Total carbon number | -CH$_2$- |
|  | Aromatic side ring | ⬡ |
|  | Naphthenic side ring | ⬡ |

FIG. 22 (Continued)

Table 5: Examples of compounds with their corresponding conceptual segments and values used in the compound selection process.

| Compound | Total carbon number | One-branch methylene | Two-branch methylene | Aromatic side ring | Naphthenic side ring |
|---|---|---|---|---|---|
| H₃C—CH₃ | 2 | 0 | 0 | 0 | 0 |
| H₃C–CH(CH₃)–CH₃ | 4 | 1 | 0 | 0 | 0 |
| (CH₃)₃C–CH₃ | 5 | 0 | 1 | 0 | 0 |
| cyclohexane | 6 | 0 | 0 | 0 | 1 |
| benzene | 6 | 0 | 0 | 1 | 0 |

FIG. 23

Table 6. Conceptual segments, their purpose, segment number range, and sample compounds that can be selected by the segment and the corresponding segment number.

| Segment Name | | Description / Purpose | Values | Examples / Segment Number | |
|---|---|---|---|---|---|
| Total carbon number | | Total carbon number. This segment dictates the carbon number distribution for a class. | [1, 2, ..., 80] |  i = 4 |  i = 5 |
| One-branch methylene | | Secondary carbon branching. This segment dictates the distribution of secondary branch points for a class. | [0, 1, 2, 3, 4] |  j = 0 | 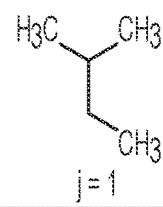 j = 1 |
| Two-branch methylene | | Tertiary carbon branching. This segment dictates the distribution of tertiary branch points for a class. | [0, 1, 2, 3] |  k = 0 | 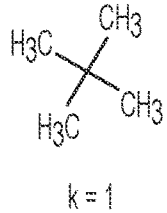 k = 1 |
| Aromatic side ring | | Aromatic ring number. This segment dictates the distribution of aromatic rings for a class. | [0, 1, 2, ..., 10] | 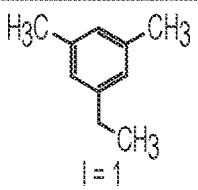 l = 1 |  l = 2 |
| Naphthenic side ring | | Naphthenic ring number. This segment dictates the distribution of naphthenic rings for a class. | [0, 1, 2, ..., 7] | 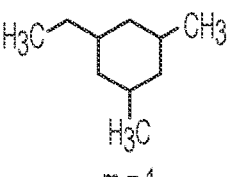 m = 1 | 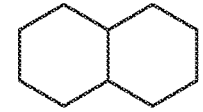 m = 2 |
| | Isomer Type Class | Mole fraction between 2 chemical isomer subclasses. This segment dictates the ratio between two subclasses sharing the same class. | | | |

FIG. 24

Table 6. Conceptual segments, their purpose, segment number range, and sample compounds that can be selected by the segment and the corresponding segment number.

| | | | | | |
|---|---|---|---|---|---|
| Mole fraction of ... | 6CR Naphthenes [HC] | 5-ring Naphthene vs. 6-ring Naphthene | [0 - 1] | x = 0 | x = 1 |
| | Paraffinic Sulfide Thiophene/ Sulfide [S2] | Naphthenic Sulfide vs. Paraffinic Sulfide | [0 - 1] | x = 0 | x = 1 |
| | SO2 Sulfoxides [S10x] | SO1 vs. SO2 | [0 - 1] | x = 0 | x = 1 |
| | Phenol Sulfur-Oxygen [S10x] | Basic Nitrogen/Ketone vs. Basic Nitrogen/Phenol | [0 - 1] | x = 0 | x = 1 |
| | Thiophene Sulfur-Oxygen [S10x] | Sulfide vs. Thiophene | [0 - 1] | x = 0 | x = 1 |
| | Paraffinic Sulfide Neutral Nitrogen-Sulfur [N1S1] | Thiophene vs. Paraffinic Sulfide | [0 - 1] | x = 0 | x = 1 |

FIG. 24 (Continued)

Table 6. Conceptual segments, their purpose, segment number range, and sample compounds that can be selected by the segment and the corresponding segment number.

| Segment | Purpose | Range | x = 0 | x = 1 |
|---|---|---|---|---|
| NO2 Neutral Nitrogen-Oxygen [N1Ox] | NO1 Neutral Nitrogen vs. NO2 Neutral Nitrogen | [0 - 1] | 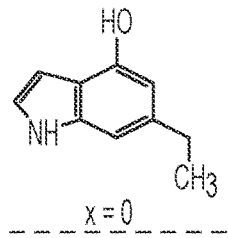 | 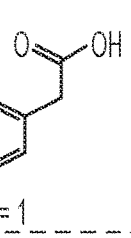 |
| Neutral Nitrogen Basic Nitrogen [N2] | 2 x Basic Nitrogen vs. Neutral Nitrogen 1/Basic Nitrogen 1 | [0 - 1] | 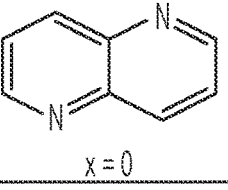 | 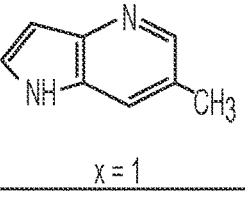 |
| Basic Nitrogen Paraffinic Sulfide Basic Nitrogen-Sulfer [N1S1] | Thiophene vs. Paraffinic Sulfide | [0 - 1] | 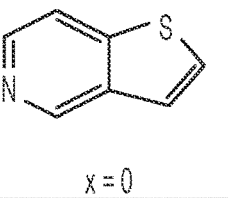 | 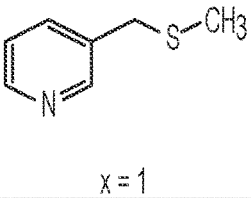 |
| NO2 Basic Nitrogen-Oxygen [N1Ox] | NO1 Basic Nitrogen vs. NO2 Basic Nitrogen | [0 - 1] | 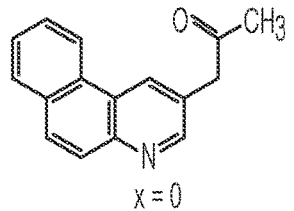 | 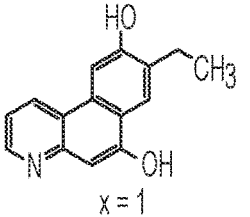 |
| Aromatic Acid Aromatic acids [O2] | Naphthenic Acid vs. Aromatic Acid | [0 - 1] | 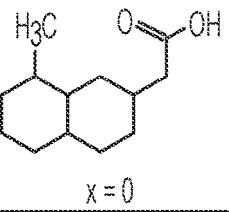 | 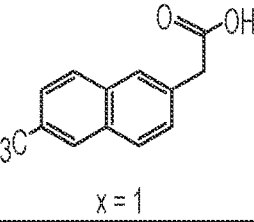 |

FIG. 24 (Continued)

Table 7: Hypothetical calculation of individual compound compositions within signal groups using a distribution function shown in FIG. 16.

| Signal Group Composition $x_{Signal\ Group}$ | Compound Assigned to Signal Group Structure | Assigned Structural Density Index [0 - n] | Structure Density Index Probability $p(c)$ | Normalized Structure Density Index Probability $\dfrac{p(c)}{\Sigma p}$ | Compound Composition $x_C$ |
|---|---|---|---|---|---|
| 0.010 (Aromatic Class, CN = 16, DBE = 9 Signal Group) | 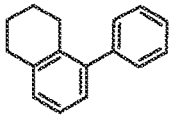 | 0 | 0.300 | 0.327 | 3.27 x 10$^{-3}$ |
| | 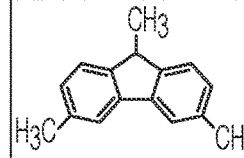 | 1 | 0.233 | 0.254 | 2.54 x 10$^{-3}$ |
| | 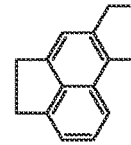 | 2 | 0.175 | 0.190 | 1.91 x 10$^{-3}$ |
| | 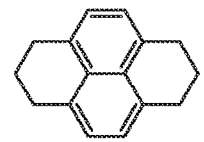 | 3 | 0.123 | 0.134 | 1.34 x 10$^{-3}$ |
| | 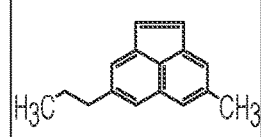 | 4 | 0.086 | 0.093 | 9.38 x 10$^{-4}$ |

FIG. 25

Table 7: Hypothetical calculation of individual compound compositions within signal groups using a distribution function shown in FIG. 16.
| 0.030 (Aromatic Class, CN = 32, DBE = 16 Signal Group) | | | | | |
|---|---|---|---|---|---|
| | 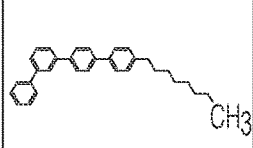 | 0 | 0.300 | 0.327 | 9.82 x 10$^{-3}$ |
| | 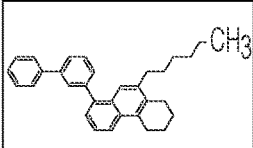 | 1 | 0.233 | 0.254 | 7.62 x 10$^{-3}$ |
| | 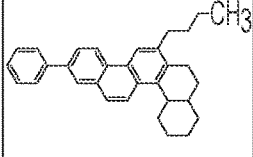 | 2 | 0.175 | 0.190 | 5.73 x 10$^{-3}$ |
| | 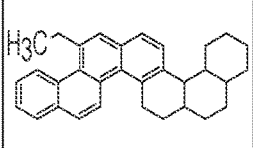 | 3 | 0.123 | 0.134 | 4.02 x 10$^{-3}$ |
| | 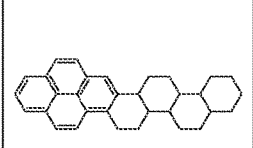 | 4 | 0.086 | 0.093 | 2.82 x 10$^{-3}$ |
FIG. 25 (Continued)

MOLECULAR CHARACTERIZATION METHOD AND SYSTEM

RELATED APPLICATION

This application claims the benefit of U.S. Provisional Application No. 62/489,087, filed on Apr. 24, 2017. The entire teachings of the above application are incorporated herein by reference.

BACKGROUND

Crude oils are complex naturally occurring materials that can vary greatly in terms of properties such as density, volatility, viscosity, sulfur content, nitrogen content and metal content, depending on geographical locations, source rocks, age and depth of formation and production. Crude oils are composed of a very large number of different molecular species. Different crude oils have different types and quantities (i.e., compositions) of molecules. AspenTech previously developed methods to represent the compositions and properties of crude oils using a molecular characterization methodology. See U.S. Pat. No. 9,934,367, issued Apr. 3, 2018, entitled "Method of Characterizing Chemical Composition Of Crude Oil For Petroleum Processing", and U.S. Patent Application Publication No. 2016/0162664, filed Feb. 18, 2016, entitled "Method To Represent Metal Content In Crude Oils, Reactor Feedstocks, And Reactor Products" (now U.S. Pat. No. 10,393,723, issued Aug. 27, 2019), which are herein incorporated by reference in their entirety.

The previous methods use traditional assay data such as distillation curves (e.g., TBP curve), density curve, sulfur curve and PNA analysis to estimate a molecular distribution for a crude oil. While those methods are substantial and significant improvements relative to the state of the art at that time, multiple solutions for the molecular distribution can exist, all of which can match the available assay data equally well. The nature of the molecular distribution can have a strong impact on a number of variables of interest in process calculations, such as reaction kinetics and pathways, and physical properties, such as cetane number, RON and viscosity. Therefore, there is a need to find a molecular distribution solution that best matches the actual molecular distribution of the crude oil.

SUMMARY OF THE INVENTION

Molecular profiles obtained by the methods described herein provide improved molecular distributions of compounds that are used to represent compositions and properties of crude oils and feedstocks. The improved distribution can more closely match experimental data on the crude or feedstock samples. A feedstock sample refers to products from a distillation column in the refinery that is fed to another unit, such as a reactor, or a petroleum fraction, which is a distilled fraction of a crude oil. Feedstock and petroleum fraction will be used interchangeably in this document.

A first embodiment of the present invention is a computer-implemented method of characterizing chemical composition of a sample containing crude oil or a petroleum fraction. The method comprises: in a processor: (i) receiving assay data comprising molecular-level assay data of the sample, or molecular-level assay data and traditional assay data of the sample; (ii) setting a) absolute compound compositions based on the molecular-level assay data of the sample, b) first compound classes and class weight(s), first conceptual segment type(s), and first segment distribution based on at least part of the molecular-level assay data, and/or c) second compound classes and class weight(s), second conceptual segment type(s), and second segment distribution based on at least part of the traditional assay data of the sample, if received; (iii) determining a) absolute compound compositions, b) first compound composition(s) from first segment distribution values, which represent the first segment distribution, and first class weight(s) set based on at least part of the molecular level data, and/or c) second compound composition(s) from second segment distribution parameters, which represent the second segment distribution, and second class weight(s) set based on the traditional assay data of the sample, if received; (iv) reconciling a) the absolute compound compositions, b) the first compound composition(s), and/or c) second compound composition(s), thereby obtaining a reconciled compound composition; and (v) adjusting, when the molecular-level assay data includes qualitative molecular level assay data and/or traditional assay data, first and second class weight(s) and segment distribution parameters until physical and/or chemical properties determined for the reconciled compound composition are consistent with corresponding received assay data, thereby obtaining a refined compound composition; thereby forming a characterization of the chemical composition of the sample.

In one aspect of the first embodiment, the molecular assay data comprises gas chromatography-mass spectrometry (GC-MS) data, gas chromatography time-of-flight spectrometry (GC-ToF) data, or Fourier transform ion cyclotron resonance mass spectrometry (FT ICR-MS) data.

In another aspect of the first embodiment or any combination of the preceding aspects, the molecular assay data is gas chromatography-mass spectrometry (GC-MS) data, gas chromatography time-of-flight spectrometry (GC-ToF) data, or Fourier transform ion cyclotron resonance mass spectrometry (FT ICR-MS) data.

In yet another aspect of the first embodiment, any of the preceding aspects, or any combination of the preceding aspects, the FT ICS-MS data is atmospheric pressure photo ionization (APPI) FT ICR-MS data, negative electrospray ionization (ESI−) FT ICR-MS data, or positive electrospray ionization (ESI+) FT ICR-MS data.

In yet another aspect of the first embodiment, any of the preceding aspects, or any combination of the preceding aspects, the GC-MS data is flame ionization detector gas chromatography (GC-FID) data.

In yet another aspect of the first embodiment, any of the preceding aspects, or any combination of the preceding aspects, the molecular level data comprises GC-MS data, and the method further comprises selecting pure compounds from a compound library based on the GC-MS data.

In yet another aspect of the first embodiment, any of the preceding aspects, or any combination of the preceding aspects, the compound identity and absolute compound composition are determined from GC-MS data.

In yet another aspect of the first embodiment, any of the preceding aspects, or any combination of the preceding aspects, the molecular level data comprises GC-ToF data, and the method further comprises transforming GC-ToF signal-strength data, GC-ToF data derived carbon number, and/or GC-ToF data derived double bond equivalent (DBE) into an Aspen distribution.

In yet another aspect of the first embodiment, any of the preceding aspects, or any combination of the preceding aspects, the method further comprises setting first compound class weight(s), first conceptual segment type(s), and first segment distribution based on an Aspen distribution determined from GC-ToF data.

In yet another aspect of the first embodiment, any of the preceding aspects, or any combination of the preceding aspects, the method further comprises determining a GC-ToF based compound composition from GC-ToF data derived class weight(s), GC-ToF data derived segment type(s), and GC-ToF data derived segment distribution values.

In yet another aspect of the first embodiment, any of the preceding aspects, or any combination of the preceding aspects, the first compound composition(s) comprises a compound composition determined from GC-ToF data, that is, a GC-ToF based compound composition.

In yet another aspect of the first embodiment, any of the preceding aspects, or any combination of the preceding aspects, the GC-ToF based compound composition is not adjusted based on any difference in physical and/or chemical property of the reconciled compound composition compared with corresponding received assay data.

In yet another aspect of the first embodiment, any of the preceding aspects, or any combination of the preceding aspects, the molecular level data comprises quantitative molecular-level assay data, and the method further comprises (1) transforming signal strength data derived from the quantitative molecular-level assay data, quantitative molecular-level assay data derived carbon number, and/or quantitative molecular-level assay data derived DBE into an Aspen distribution; (2) setting first compound class weight(s), first conceptual segment type(s), and first segment distribution based on an Aspen distribution determined from the quantitative molecular-level assay data; and (3) computing a compound composition from quantitative molecular-level assay data derived class weight(s), quantitative molecular-level assay data derived segment type(s), and quantitative molecular-level assay data derived segment distribution values.

In yet another aspect of the first embodiment, any of the preceding aspects, or any combination of the preceding aspects, the molecular level data comprises FT-ICR-MS data, and the method further comprises transforming FT ICR-MS signal-strength data, FT ICR-MS derived formula, FT ICR-MS derived carbon number, and/or FT ICR-MS derived DBE into an Aspen distribution, a Gamma distribution, and/or uniform segment distribution.

In yet another aspect of the first embodiment, any of the preceding aspects, or any combination of the preceding aspects, the method further comprises setting the first compound class weight(s), the first conceptual segment type(s), and the first segment distribution based on a FT ICR-MS data derived Aspen distribution, Gamma distribution, and/or uniform segment distribution.

In yet another aspect of the first embodiment, any of the preceding aspects, or any combination of the preceding aspects, the method further comprises determining a FT ICR-MS based compound composition from FT ICR-MS data derived class weight(s), FT ICR-MS data derived segment type(s), and FT ICR-MS data derived segment distribution values and/or parameters. In a specific aspect of this aspect, the FT ICR-MS based compound composition is adjusted based on any difference in physical and/or chemical property of the reconciled compound composition compared with corresponding received assay data.

In yet another aspect of the first embodiment, any of the preceding aspects, or any combination of the preceding aspects, the molecular level data comprises qualitative molecular-level assay data, and the method further comprises (1) transforming signal strength data derived from the qualitative molecular-level assay data, qualitative molecular-level assay data derived formula, qualitative molecular-level assay data derived carbon number, and/or qualitative molecular-level assay data derived DBE into an Aspen distribution, a Gamma distribution, and/or uniform segment distribution; (2) setting first compound class weight(s), first conceptual segment type(s), and first segment distribution based on a qualitative molecular-level assay data derived Aspen distribution, Gamma distribution, and/or uniform segment distribution; and (3) computing a compound composition from qualitative molecular-level assay data derived class weight(s), qualitative molecular-level assay data derived segment type(s), and qualitative molecular-level assay data derived segment distribution values and/or parameters.

In yet another aspect of the first embodiment, any of the preceding aspects, or any combination of the preceding aspects, the first compound composition(s) comprises a compound composition determined from FT ICR-MS data, that is, a FT ICR-MS based compound composition. In a specific aspect of this aspect, the FT ICR-MS based compound composition is adjusted based on any difference in physical and/or chemical property of the reconciled compound composition compared with corresponding received assay data.

In yet another aspect of the first embodiment, any of the preceding aspects, or any combination of the preceding aspects, the first compound composition is a FT ICR-MS based compound composition and the second compound composition is determined from traditional assay data.

In yet another aspect of the first embodiment, any of the preceding aspects, or any combination of the preceding aspects, only the FT ICR-MS based compound composition and the second compound composition are adjusted until physical and/or chemical properties determined for the reconciled compound composition are consistent with corresponding received assay data.

In yet another aspect of the first embodiment, any of the preceding aspects, or any combination of the preceding aspects, the received assay data comprises traditional assay data.

In yet another aspect of the first embodiment, any of the preceding aspects, or any combination of the preceding aspects, the traditional assay data comprises one or more of distillation curve data, density curve data, sulfur curve data, basic nitrogen curve data, total nitrogen curve data, carbon-to-hydrogen ratio curve data, total acid number curve data, PIONA content curve data, viscosity curve data, nickel content curve data, and vanadium content curve data.

In yet another aspect of the first embodiment, any of the preceding aspects, or any combination of the preceding aspects, the first and second compound classes comprise, independently, one or more of a paraffin class, a naphthene class, an aromatic class, an olefin class, a mercaptan class, a thiophene or sulfide class having a single sulfur atom class, a thiophene and sulfide class having two sulfur atoms, a sulfoxide class, a sulfur-oxygen class, a neutral nitrogen having a single pyrrole class, a neutral nitrogen class having two pyrrole nitrogens class, a neutral nitrogen-sulfur class, a neutral nitrogen-oxygen class, a basic nitrogen having a single pyridine class, a basic nitrogen having a pyridine and either another pyridine or a pyrrole class, a basic nitrogen-sulfur class, a basic nitrogen-oxygen class, a phenol class, a paraffinic acid class, an aromatic and naphthenic acid class, a nickel porphyrin class, and a vanadium porphyrin class.

In yet another aspect of the first embodiment, any of the preceding aspects, or any combination of the preceding aspects, the first and second compound classes comprise a paraffin class, a naphthene class, an aromatic class, an olefin class, a mercaptan class, a thiophene or sulfide class having a single sulfur atom class, a thiophene and sulfide class having two sulfur atoms, a sulfoxide class, a sulfur-oxygen class, a neutral nitrogen having a single pyrrole class, a neutral nitrogen class having two pyrrole nitrogens class, a neutral nitrogen-sulfur class, a neutral nitrogen-oxygen class, a basic nitrogen having a single pyridine class, a basic nitrogen having a pyridine and either another pyridine or a pyrrole class, a basic nitrogen-sulfur class, a basic nitrogen-oxygen class, a phenol class, a paraffinic acid class, an aromatic and naphthenic acid class, a nickel porphyrin class, and a vanadium porphyrin class.

In yet another aspect of the first embodiment, any of the preceding aspects, or any combination of the preceding aspects, the conceptual segment types for the paraffin class comprise total carbon number, one-branch methylene, and two-branch methylene.

In yet another aspect of the first embodiment, any of the preceding aspects, or any combination of the preceding aspects, the conceptual segment types for the naphthene classes comprise total carbon number, naphthenic side ring, and mole fraction of six-membered rings versus five-membered rings.

In yet another aspect of the first embodiment, any of the preceding aspects, or any combination of the preceding aspects, the conceptual segment types for the aromatic class comprise total carbon number, aromatic side ring, and naphthenic side ring.

In yet another aspect of the first embodiment, any of the preceding aspects, or any combination of the preceding aspects, the molecular level data is obtained from the sample in its entirety.

In yet another aspect of the first embodiment, any of the preceding aspects, or any combination of the preceding aspects, the molecular level data is obtained from one or more cuts of the sample.

In yet another aspect of the first embodiment, any of the preceding aspects, or any combination of the preceding aspects, the method further comprises outputting the characterization of the chemical composition of the sample containing crude oil or a petroleum fraction.

In yet another aspect of the first embodiment, any of the preceding aspects, or any combination of the preceding aspects, the sample is a crude oil or a petroleum fraction.

In yet another aspect of the first embodiment, any of the preceding aspects, or any combination of the preceding aspects, FT ICR-MS data and traditional data are received.

In yet another aspect of the first embodiment, any of the preceding aspects, or any combination of the preceding aspects, at least two of GC-MS data, GC-ToF data, FT ICR-MS data and traditional assay data are received.

In yet another aspect of the first embodiment, any of the preceding aspects, or any combination of the preceding aspects, at least three of GC-MS data, GC-ToF data, FT ICR-MS data and traditional assay data are received.

In yet another aspect of the first embodiment, any of the preceding aspects, or any combination of the preceding aspects, GC-MS data, GC-ToF data, FT ICR-MS data and traditional assay data are received.

In yet another aspect of the first embodiment, any of the preceding aspects, or any combination of the preceding aspects, qualitative molecular-level assay data and traditional assay data are received.

In yet another aspect of the first embodiment, any of the preceding aspects, or any combination of the preceding aspects, at least two of exact assay data, quantitative molecular-level assay data, qualitative molecular-level assay data and traditional assay data are received.

In yet another aspect of the first embodiment, any of the preceding aspects, or any combination of the preceding aspects, at least three of exact assay data, quantitative molecular-level assay data, qualitative molecular-level assay data and traditional assay data are received.

In yet another aspect of the first embodiment, any of the preceding aspects, or any combination of the preceding aspects, exact assay data, quantitative molecular-level assay data, qualitative molecular-level assay data and traditional assay data are received.

In yet another aspect of the first embodiment, any of the preceding aspects, or any combination of the preceding aspects, the method further comprises estimating physical or chemical properties for the sample as a function of the characterized chemical composition of the sample.

In yet another aspect of the first embodiment, any of the preceding aspects, or any combination of the preceding aspects, the estimated physical properties of the sample include one or more of normal boiling point, liquid density, liquid viscosity, Conradson Carbon residue, research octane number, motor octane number, cetane number, and Reid vapor pressure.

In yet another aspect of the first embodiment, any of the preceding aspects, or any combination of the preceding aspects, estimating chemical properties of the sample comprises calculating from the chemical formula, chemical structure and chemical compositions, including sulfur content, basic nitrogen content, total nitrogen content, carbon content, hydrogen content, carbon to hydrogen ratio, nickel content, vanadium content, oxygen content, paraffin content, isoparaffin content, olefin content, naphthene content, and aromatic content.

In yet another aspect of the first embodiment, any of the preceding aspects, or any combination of the preceding aspects, traditional assay data is received.

In yet another aspect of the first embodiment, any of the preceding aspects, or any combination of the preceding aspects, the method further comprises providing a library of model compounds.

In yet another aspect of the first embodiment, any of the preceding aspects, or any combination of the preceding aspects, the method comprises assigning a signal group for one or more model compounds from the library of model compounds.

In yet another aspect of the first embodiment, any of the preceding aspects, or any combination of the preceding aspects, the method further comprises assigning a signal group for one or more model compounds from a library of model compounds.

In yet another aspect of the first embodiment, any of the preceding aspects, or any combination of the preceding aspects, the model compounds from the library of model compounds, which correspond to one signal group, have the same class, the same carbon number and the same double bond equivalent.

In yet another aspect of the first embodiment, any of the preceding aspects, or any combination of the preceding aspects, the sample comprises compounds having i) different carbon numbers from between 1 and 100, and ii) different double bond equivalent numbers from 0 to 50.

In yet another aspect of the first embodiment, any of the preceding aspects, or any combination of the preceding aspects, the assay data that is received comprises molecular-level assay data comprising exact data, and, the method further comprises, assigning, on the basis of the exact data, one model compound to a specific signal group.

In yet another aspect of the first embodiment, any of the preceding aspects, or any combination of the preceding aspects, the assay data that is received comprises molecular-level assay data comprising exact lump data, and, the method further comprises, assigning, on the basis of the exact lump data, a plurality of model compounds to a signal group, the model compounds having the same class and same carbon number.

In yet another aspect of the first embodiment, any of the preceding aspects, or any combination of the preceding aspects, the assay data that is received comprises quantitative molecular-level assay data, and, the method further comprises, assigning, on the basis of the quantitative molecular-level assay data, a plurality of model compounds to a signal group, the model compounds having the same class, same carbon number and same double bond equivalent.

In yet another aspect of the first embodiment, any of the preceding aspects, or any combination of the preceding aspects, the assay data that is received comprises qualitative molecular-level assay data, and, the method further comprises, assigning, on the basis of the qualitative molecular-level assay data, a plurality of model compounds to a signal group, the model compounds having the same class, same carbon number and same double bond equivalent when the Aspen distribution is used to represent at least part of the data, and, the method further comprises, assigning, on the basis of the qualitative molecular-level assay data, a plurality of model compounds to a signal group, the model compounds having the same class, same carbon number, same one-branch methylene number, same two-branch methylene number, same aromatic side ring number, and same naphthenic side ring number when the Gamma distribution or uniform distribution is used to represent at least part of the data.

In yet another aspect of the first embodiment, any of the preceding aspects, or any combination of the preceding aspects, the assay data that is received comprises traditional assay data, and, the method further comprises, assigning, on the basis of the traditional assay data, a plurality of model compounds to a signal group, the model compounds having the same class, same carbon number, same one-branch methylene number, same two-branch methylene number, same aromatic side ring number, and same naphthenic side ring number.

In yet another aspect of the first embodiment, any of the preceding aspects, or any combination of the preceding aspects, in assigning one or more model compounds to a signal group, exact data has higher priority than exact lump data, exact lump data has higher priority than quantitative molecular-level assay data, quantitative molecular-level data has higher priority than qualitative molecular-level assay data, and qualitative molecular-level assay data has higher priority than traditional assay data; and wherein, when assay data of differing priority exists which each would allow assigning a model compound to a signal group, assay data with highest priority is used to assign the model compound to the signal group.

In yet another aspect of the first embodiment, any of the preceding aspects, or any combination of the preceding aspects, the assay data that is received comprises molecular-level assay data comprising exact data, and, the method further comprises, assigning, on the basis of the exact data, a first model compound to a first signal group.

In yet another aspect of the first embodiment, any of the preceding aspects, or any combination of the preceding aspects, the assay data that is received comprises molecular-level assay data comprising exact lump data, and, the method further comprises, assigning, on the basis of the exact lump data, a plurality of model compounds to a signal group to which model compounds have not been assigned on the basis of exact data, the model compounds being assigned to the signal group having the same class, and same carbon number.

In yet another aspect of the first embodiment, any of the preceding aspects, or any combination of the preceding aspects, the assay data that is received comprises quantitative molecular-level assay data, and, the method further comprises, assigning, on the basis of the quantitative molecular-level assay data, a plurality of model compounds to a signal group to which model compounds have not been assigned on the basis of exact data or exact lump data, the model compounds being assigned to the signal group having the same class, same carbon number and same double bond equivalent.

In yet another aspect of the first embodiment, any of the preceding aspects, or any combination of the preceding aspects, the assay data that is received comprises qualitative molecular-level assay data, and, the method further comprises, assigning, on the basis of the qualitative molecular-level assay data, a plurality of model compounds to a signal group to which model compounds have not been assigned on the basis of exact data, exact lump data or quantitative molecular-level assay data, the model compounds being assigned to the signal group having the same class, same carbon number and same double bond equivalent when the Aspen distribution is used to represent at least part of the qualitative molecular-level assay data, and, the method further comprises, assigning, on the basis of the qualitative molecular-level assay data, a plurality of model compounds to a signal group to which model compounds have not been assigned on the basis of exact data, exact lump data, quantitative molecular-level assay data, or at least part of the qualitative molecular-level assay data that uses the Aspen distribution, the model compounds having the same class, same carbon number, same one-branch methylene number, same two-branch methylene number, same aromatic side ring number, and same naphthenic side ring number.

In yet another aspect of the first embodiment, any of the preceding aspects, or any combination of the preceding aspects, the assay data that is received comprises traditional assay data, and, the method further comprises, assigning, on the basis of the traditional assay data, a plurality of model compounds to a signal group to which model compounds have not been assigned on the basis of exact data, exact lump data, quantitative molecular-level assay data or qualitative molecular-level assay data, the model compounds being assigned to the signal group having the same class, same carbon number, same one-branch methylene number, same two-branch methylene number, same aromatic side ring number, and same naphthenic side ring number.

In yet another aspect of the first embodiment, any of the preceding aspects, or any combination of the preceding aspects, the method further comprises calculating compound compositions within a signal group using a probability distribution function that describes the structural density index of constituent compounds within signal groups belonging to a cut of the sample.

In yet another aspect of the first embodiment, any of the preceding aspects, or any combination of the preceding aspects, the method further comprises calculating compound compositions within a signal group using a probability distribution function that describes the structural density index of constituent compounds within all signal groups in the sample.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 8 is an example of assay data for a crude, showing type(s) of data that have been measured for the constituent petroleum fractions of the crude, the level of molecular details for each data type and the priority given to the data type during the reconciliation step of the characterization process.

FIG. 19 is a table (Table 1) of example compound classes that may be used in embodiments to represent species in a sample containing crude oil or a petroleum fraction.

FIG. 20 is a table (Table 2) of examples of molecules, their PC-SAFT functional groups, and the frequency of each functional group, according to an embodiment FIG. 21 is a table (Table 3) of PC-SAFT functional groups that may be utilized in embodiments.

FIG. 22 is a table (Table 4) of conceptual segment types and segment structures representing compound classes in Table 1 of FIG. 19.

FIG. 23 is a table (Table 5) of examples of compounds with their corresponding conceptual segments and values used in a compound selection process according to an embodiment.

FIG. 24 is a table (Table 6) of conceptual segments, their purpose, segment number range, and sample compounds that can be selected by the segment and the corresponding segment number in embodiments.

FIG. 25 is a table (Table 7) illustrating a hypothetical calculation of individual compound compositions within signal groups using a distribution function shown in FIG. 16.

DETAILED DESCRIPTION OF THE INVENTION

A description of example embodiments of the invention follows.

Figure 1A:
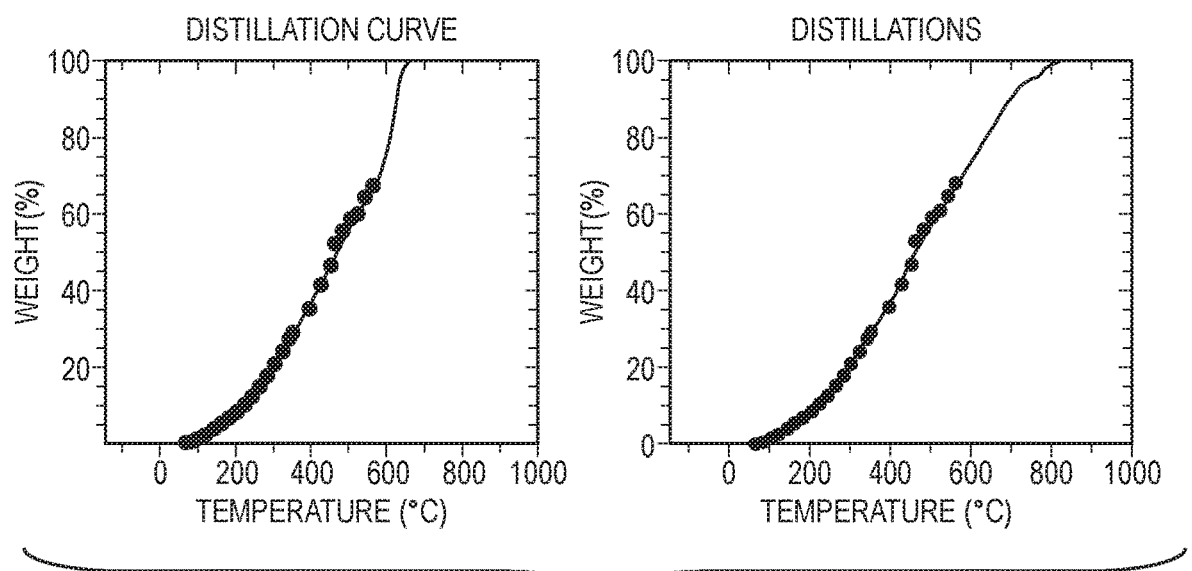
FIG. 1A provides two distillation curves including experimental data (circles) and fitted data (solid curves), Solution 1 on the left side and Solution 2 on the right side.
Figure 1B:
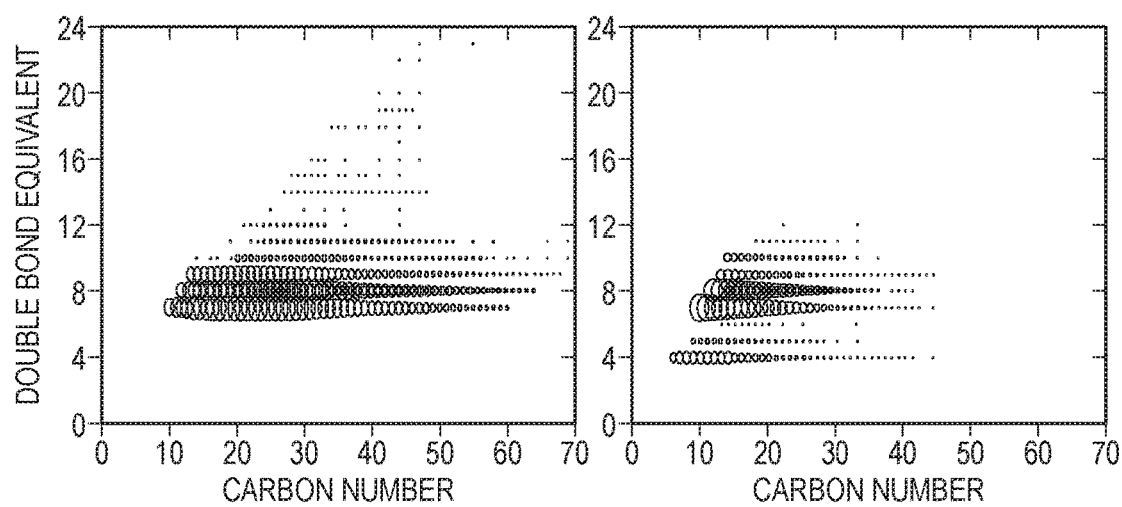
FIG. 1B provides two plots of double bond equivalent (DBE) vs. carbon number; the plot on the left is the plot corresponding to Solution 1 in FIG. 1A, and the plot on the right is the plot corresponding to Solution 2 in FIG. 1A.

Prior methods of characterizing the chemical composition of crude oil, such as those described in U.S. Pat. No. 9,934,367, issued Apr. 3, 2018 and U.S. Patent Application Publication No. 2016/0162664 (now U.S. Pat. No. 10,393,723, issued Aug. 27, 2019), use traditional assay data, such as distillation curves. While such methods provide accurate results, there is still room for improvements. One potential drawback is that multiple solutions for the molecular distribution can exist, all of which can match the available assay data equally well. FIG. 1A provides two graphs, one entitled Solution 1 on the left hand side and one entitled Solution 2 on the right hand side. The two graphs contain the same experimental distillation data (shown as circles), but show different calculated curves fitted to the experimental data. The calculations were performed using the method described in U.S. Pat. No. 9,934,367 and U.S. Patent Application Publication No. 2016/0162664 (now U.S. Pat. No. 10,393,723, issued Aug. 27, 2019). Both solutions match distillation curve data equally well in the range of available data. FIG. 1B shows molecular distributions, as represented by plots of the double-bond equivalent (DBE) vs. carbon number. DBE is a prior art known measure of the number of double bonds and rings present in a compound. For example, benzene has a DBE of four. Tetralin has a DBE of five. Naphthalene has a DBE of 7. The dot size in FIG. 1B denotes relative composition of the compound (larger dot=higher composition). For example, in Solution 1, naphthalene compounds (DBE=7) with varying length of methyl side chain (1 to 50) are present, with maximum composition around total carbon number of 20. No benzene compounds are included in Solution 1, as can be seen from the absence of any dots on the DBE=4 line. In Solution 2, naphthalene compounds have shorter side-chain distribution (1-20) and, among other compounds, benzene compounds and some tetralin structures (DBE=5) are also used. The two solutions represent different molecular constituents, which can significantly influence reaction kinetics and pathways and physical properties, such as cetane number, research octane number (RON), and viscosity.

The methods described herein can improve upon prior methods, for example, by incorporating molecular level data obtained using advanced analytical techniques such as mass spectrometry data.

Segments and Classes

The molecular characterization methods described herein use a set of compounds to represent the species in a sample containing crude oil or a petroleum fraction. Those compounds are categorized into compound classes (also referred to herein as "molecular classes"). Table 1 in FIG. 19 shows example compound classes, though additional classes can also be utilized. For each class, sample compounds are provided for illustrative purposes.

The methods of the present invention can make use of one or more of the compound classes listed in Table 1 of FIG. 19. Typically, at least the first three compound classes are used as they are typically the most prevalent in the sample. The compound classes used depend on the types of data available. For example, if Nickel and Vanadium content data are available, classes 21 and 22 will be used. In a preferred embodiment of the present invention, all of compound classes in Table 1 of FIG. 19 are used.

Consideration of Isomers

Figure 2:
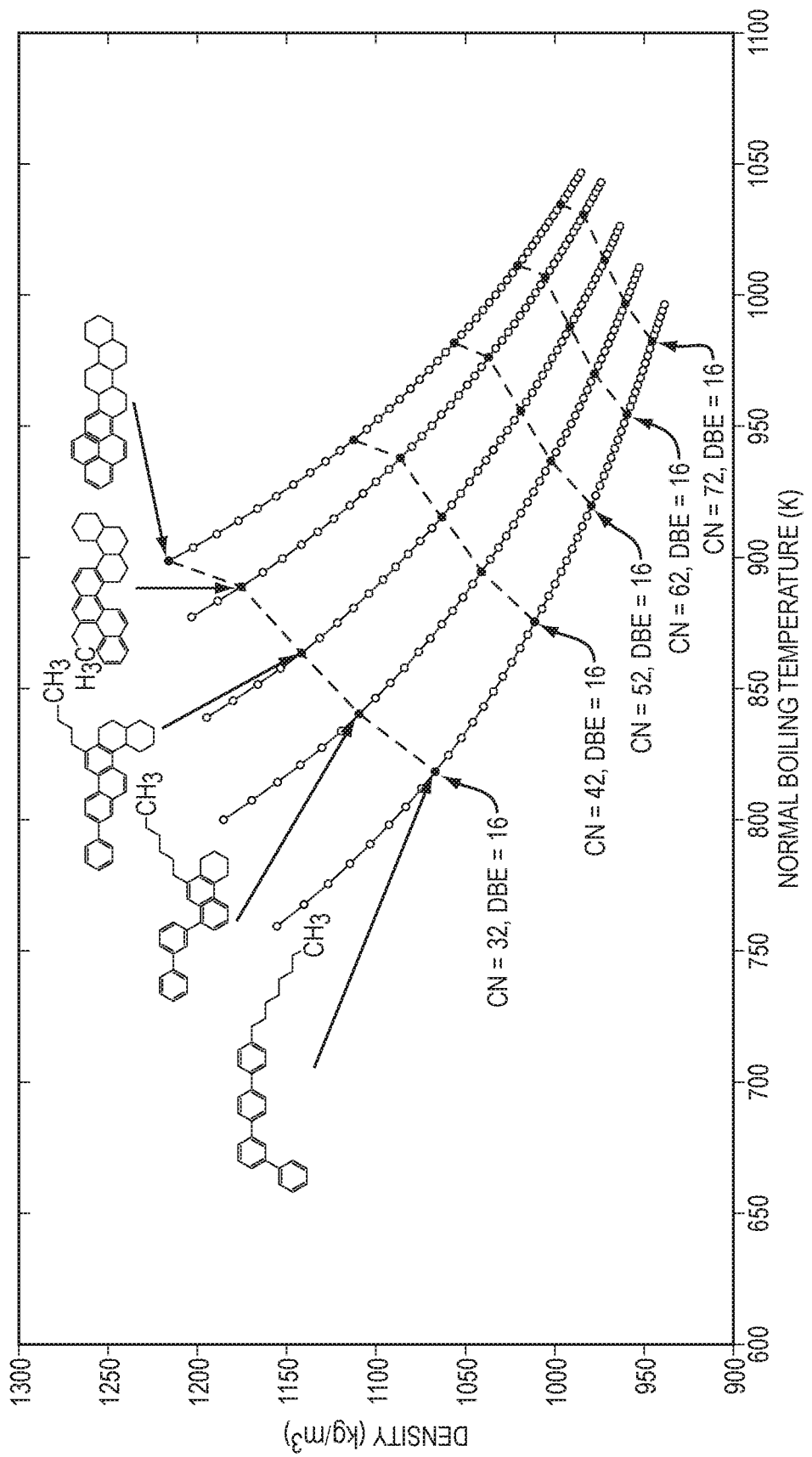
FIG. 2 is a plot of density as a function of normal boiling temperature for five homologous series of compounds, with different numbers of aromatic and naphthenic rings, and lengths of hydrocarbon side chain. The dash lines show isomers with the same total carbon number (CN) and double bond equivalent (DBE). Example compounds are given for CN=32 and DBE=16.

Structural isomers are compounds that belong to the same class, and have the same chemical formula. However, they may differ in double bond equivalents, branching, ring structure, aromatic content, and naphthenic content. Due to these differences, their physical properties also differ. As an illustration, FIG. 2 shows a plot of density as a function of normal boiling temperature for five homologous series of compounds, with different numbers of aromatic and naphthenic rings, and lengths of hydrocarbon side chain. The dash lines show isomers with the same total carbon number (CN) and double bond equivalent (DBE). For example, the top-most dash line corresponds to isomers with CN=32 and DBE=16. The properties (e.g., density and normal boiling temperatures) of these isomers differ significantly.

Compounds Library

A library of model compounds can be formed covering the 22 compound classes shown in Table 1 of FIG. 19. The compounds were selected considering their thermodynamic stability and that their structures have been identified to exist or likely to exist in crude oils, feed stocks, and reactor products [See e.g. Linzhou Zhang, et al. "Molecular Representation of Petroleum Vacuum Resid," *Energy Fuels*, 28(3):1736-1749 (2013)]. Structural isomers are included. A library of ~54,000 compounds was used in the current work and is referred to herein as "MC Library." The library of model compounds is not limited to a particular number of compounds; however, typically, a larger number of model compounds that have been identified to exist or likely to exist in crude oils, feed stocks, and reactor products is desirable.

The library of model compounds used in the methods disclosed herein can also include pure compounds. For example, the library of model compounds can include between 100 and 1000 pure compounds and lumps. Typically, those compounds have a boiling point below 413.42° C.

The MC Library also comprises ~550 pure compounds and lumps in the light-end and naphtha range (compounds with a boiling point below 413.42° C.). The pure compounds are defined components, not model compounds, with properties determined from experimental measurements. Lumps are aggregates of many compounds that are structural isomers; they have the same chemical formula and belong to the same class, such as C6-isoparaffins, C7-naphthenes, or 8-carbon-aromatics. Properties of a lump are average of the properties of the constituent compounds.

Properties Estimation

Normal boiling points and liquid densities of the compounds in the MC Library can be calculated using the PC-SAFT equation of state, as described in U.S. Pat. No. 9,934,367 and U.S. Patent Application Publication No. 2016/0162664 (now U.S. Pat. No. 10,393,723, issued Aug. 27, 2019). Elemental properties, such as sulfur content, nitrogen content, carbon content and hydrogen content are calculated directly from the molecular formula, as known in the art. Other physical properties can be estimated using various prior art known correlations.

All desired molecules in the MC Library can be broken down into PC-SAFT functional groups. The frequencies of each functional group in the molecule can be identified. Each functional group has a unique set of parameters for use in estimating normal boiling point and liquid density. The functional group parameters utilized are identified through data regression against available data including saturated liquid density, liquid vapor pressure and liquid heat capacity. The data sets used in the regression include a wide range of compounds representative of compound classes and functional groups in Table 1 of FIG. 19 and Table 3 of FIG. 21. The functional group frequency and the corresponding parameters can be used to calculate the properties of the molecule. For example, normal paraffins contain two types of functional groups, namely methyl (—CH3) and methylene (>CH2) groups. As a specific example, n-butane contains two methyl groups and two methylene groups. Aromatic molecules can be described using ACH and PACC functional groups, for example, Naphthalene contains 8 ACH functional groups and 1 PACC functional group. Table 2 in FIG. 20 shows examples of molecules, their PC-SAFT functional groups, and the frequency of each functional group. Table 3 in FIG. 21 lists the PC-SAFT functional groups that have been used.

Estimation of pure compound properties for compounds in MC Library are described below:

The pure compound i can be identified by its chemical formula

Chemical Formula$_i$=C$_x$H$_y$S$_z$N$_l$O$_m$V$_n$Ni$_j$

Where,
C$_x$=Number of carbon atoms
H$_y$=Number of hydrogen atoms
S$_z$=Number of sulfur atoms
N$_l$=Number of nitrogen atoms
O$_m$=Number of oxygen atoms
V$_n$=Number of vanadium atoms
Ni$_j$=Number of nickel atoms A) Pure Compound Molecular Weight, Da $MW_i=12.011C_x+1.00794H_y+32.066S_z+14.00674N_l+15.9994O_m+50.94V_n+58.7Ni_j$ B) Carbon Content, Wt %

$$\text{C wt \%}_i = \frac{12.011C_x}{MW_i}$$

C) Hydrogen Content, Wt %

$$\text{H wt \%}_i = \frac{1.0079H_y}{MW_i}$$

D) Sulfur Content, Wt %

$$\text{S wt \%}_i = \frac{32.066S_z}{MW_i}$$

E) Nitrogen Content, Wt %

$$\text{N wt \%}_i = \frac{14.00674N_l}{MW_i}$$

F) Oxygen Content, Wt %

$$\text{O wt \%}_i = \frac{14.00674O_m}{MW_i}$$

G) Vanadium Content, Wt %

$$\text{V wt \%}_i = \frac{50.94V_n}{MW_i}$$

H) Nickel Content, Wt %

$$\text{Ni wt \%}_i = \frac{58.7Ni_j}{MW_i}$$

I) Normal Boiling Temperature

PC-SAFT equation of state can be used to calculate the normal boiling points of all compounds in the MC Library.

J) Liquid Density

The liquid densities of all compounds in the MC Library at different temperatures can be estimated by PC-SAFT equation of state and correlated to temperature using the following correlation:

$$\rho_i = A_i + B_i \cdot T + C_i \cdot T^2$$

Where,
$\rho_i$=Liquid Density of the compound i in kg/m$^3$
$A_i$, $B_i$, $C_i$=Liquid Density Parameters for compound i
T=Temperature in K K) Liquid Viscosity A group contribution method can be used to estimate pure compound liquid viscosities. The contribution viscosity of all functional groups are regressed against available experimental liquid viscosity data. The data sets used in regression can include a wide range of compounds representative of compound classes and functional groups in Table 1 of FIG. 19 and Table 3 of FIG. 21.

$$\ln \eta_i = \sum_j v_j \cdot \ln \eta_j + x_{PACC,i} \cdot \left(-11.6705 + \frac{664.802}{(T-100)} + 2.2334 \cdot \ln T\right)$$

$$\ln \eta_j = A_j + \frac{B_j}{T} + C_j \cdot \ln T$$

Where,
$\eta_i$=The liquid viscosity of pure compound i in Pa·s
$\eta_j$=The contribution viscosity of group j in Pa·s
$v_j$=The frequency of group j in compound i
$A_j$, $B_j$, $C_j$=The liquid viscosity parameters for group j
$x_{PACC,i}$=The frequency of the PACC functional group in compound i
T=Temperature in K L) Conradson Carbon Residue:

Conradson carbon residue in wt % for pure compound $CCR_i$ can be estimated from the Pendant—Core model. The model assumes that a compound is made up of two constituents: a pendant block, which forms the distillable liquid in the pyrolysis process, and a core block, which forms the carbon residue.

A compound's core block is made up of polycyclic aromatic hydrocarbons; therefore, CCR for saturates (paraffins and naphthenes) are zero. Since the experimental measurement to determine CCR is conducted at 315° C., the CCR for compounds with normal boiling point below 315° C. are assumed to be zero. For the remaining compounds, CCR is calculated using the following formula:

$$CCR_i = 100 \frac{H_p - H_i}{H_p - H_c}; \text{ for } H_c < H_i < H_p$$

$$CCR_i = 0; \text{ for } H_i \geq H_p$$

$$CCR_i = 100; H_i \leq H_c$$

Where,
$H_i$=The hydrogen content of the compound i
$H_p$=The hydrogen content of the pedant block (11.6 wt %)
$H_c$=The hydrogen content of the core block (3.8 wt %)

Considering that compounds may be evaporated out before the thermolysis reaction during the carbon residue measurement, an evaporation effect factor can be applied to the CCR values calculated from P-C model. This factor can be assumed to be an integral normal distribution of the compound boiling points.

$$EF_i = \int_{-\infty}^{TB_i} \frac{1}{\sqrt{2\pi(TB_s)}} e^{-\frac{(TB_i - TB_m)^2}{2(TB_s)^2}}$$

Where,
$EF_i$=Evaporation factor of compound i
$TB_i$=True boiling point of compound i, ° F.
$TB_m$=Mean boiling point (1060.9° F.)
$TB_s$=Temperature standard deviation (70° F.)
M) Gross Heating Value & Net Heating Value
Both properties are closely related to the elemental content and can be calculated using the following equations:

$$GHV_i = (83.22 * C_i \% + 276.48 * H_i \% - 25.8 * O_i \% + 25 * S_i \% + 15 * N_i \%)$$

$$NHV_i = \left(\frac{GHV_i}{1000} - 0.22 * H_i \%\right) * 1000$$

Where for compound i,
$GHV_i$=Gross heating value, kJ/kg
$NHV_i$=Net heating value, kJ/kg
$c_i$=Carbon content, wt %
$H_i$=Hydrogen content, wt %=
$O_i$=Oxygen content, wt %
$S_i$=Sulfur content, wt %
$N_i$=Nitrogen content, wt %

In one embodiment the methods of the present invention use a predicted composition of the MC Library compounds to estimate crude and petroleum fraction mixture properties. Several of the estimated mixture property calculations are described below:

A) Crude and Petroleum Fraction Mass Density
Mass density of a crude or petroleum fraction is calculated as follows:

$$\frac{1}{\rho} = \sum_i \frac{w_i}{\rho_i}$$

Where,
$\rho$=Mass density in kg/m³
$w_i$=Weight fraction of compound i in the mixture
$\rho_i$=Mass density for the pure compound i in kg/m³

B) Crude and Petroleum Fraction Liquid Viscosity
Dynamic liquid viscosity of a crude or petroleum fraction can be calculated using the following equation:

$$\ln\eta = \sum_i w_i \cdot \ln\eta_i +$$

$$k_0 \cdot w_{Pl} \cdot w_{NA} + \left[k_1 + k_2 \cdot \left(\frac{1}{T} - \frac{1}{T_0}\right) + k_3 \cdot w_{AS}\right] \cdot w_{AS} \cdot (1 - w_{AS}) \ln\eta_{ij}$$

$$\ln\eta_{ij} = \frac{|\ln\eta_{AS} - \ln\eta_{non-AS}|}{2}$$

$$\ln\eta_{AS} = \sum_i w_{AS,i} \cdot \ln\eta_{AS,i}$$

$$\ln\eta_{non-AS} = \sum_j w_{non-AS,j} \cdot \ln\eta_{non-AS,j}$$

$$\sum_i w_{AS,i} = 1$$

$$\sum_j w_{non-AS,j} = 1$$

Where,
$\eta$=Mixture viscosity in Pa s
$\eta_i$=Viscosity for pure compound i in Pa s
$w_1$=Weight fraction of compound i in the mixture
$w_{Pl}$=Summation of weight fractions of normal paraffin compounds and isoparaffin compounds in the mixture
$w_{NA}$=Summation of weight fractions of naphthenic compounds (N) and aromatic compounds (A) in the mixture
$k_0$=Interaction parameter between paraffins and N+A
$k_1$, $k_2$, $k_3$=Interaction parameters between asphaltenes and all other compounds
T=Temperature in K
$T_0$=298.15K, the reference temperature
$w_{AS}$=Weight fraction of Asphaltenes in the mixture
$\eta_{AS}$=Viscosity of hypothetical mixture containing only asphaltene compounds
$w_{AS,i}$=Weight fraction of asphaltene compound i in the hypothetical mixture
$\eta_{AS,i}$=Viscosity of asphaltene compound i
$\eta_{non-AS,j}$=Viscosity of a system with all the compounds except asphaltenes
$w_{non-AS,j}$=Weight fraction of a non-asphaltene compound j in the non-asphaltenes mixture
$\eta_{non-AS,j}$=Viscosity of a non-asphaltene compound j
Kinematic viscosity is calculated from dynamic viscosity and density:

$$v = \frac{\eta}{\rho} \times 10^6$$

Where,
v=Kinematic Viscosity for a mixture in cSt
$\eta$=Dynamic Viscosity for a mixture in Pa·s
$\rho$=Mass Density of a mixture in kg/m³

C) Crude and Petroleum Fraction Molecular Weight, Da
The Molecular Weight of a crude oil or a petroleum fraction can be calculated as follows:

$$MW = \Sigma MW_i \cdot X_i$$

Where,
MW=Molecular weight of crude oil or petroleum fraction
$MW_i$=Molecular weight of compound
$X_i$=Mole fraction of compound i in the mixture D) Crude and Petroleum Fraction Total Acid Number (TAN)
Total acid number is defined as the mass of KOH in mg used to neutralize acids in 1 g oil or petroleum fraction. It can be calculated using the following equation:

$$TAN = 1/MW * \Sigma X_i^{Acid\ comps} * MW_{KOH} * 1000$$

Where,
TAN=Total acid number of the mixture, mg KOH/g
MW=Molecular weight of the mixture
$X_i^{Acid\ comps}$=Mole fraction of acid compound i in the mixture
$MW_{KOH}$ Molecular weight of KOH (56.1049 g/mol)

E) Crude and Petroleum Fraction Conradson Carbon Residue

CCR of the whole crude or petroleum fraction can be calculated as follows:

$$CCR = \sum_i w_i CCR_i * EF_i$$

Where,
$w_i$=Weight fraction of compound i in the mixture
$CCR_i$=Conradson carbon residue of compound i
$EF_i$=Evaporation factor of compound i F) Crude and Petroleum Fraction Gross Heating Value & Net Heating Value Gross and net heating values of crude and petroleum fraction can be calculated as follows:

$$GHV = \sum_i w_i * GHV_i$$

$$NHV = \sum_i w_i * NHV_i$$

Where,
GHV=Gross heating value for mixture, kJ/kg
NHV=Net heating value for mixture, kJ/kg
$w_i$=Weight fraction of compound i in mixture
$GHV_i$=Gross heating value of compound i, kJ/kg
$NHV_i$=Net heating value of compound i, kJ/kg G) Crude or Petroleum Fraction Total Sulfur Content $TS = \Sigma w_{i,} \cdot S_i$ Where,
TS=Total sulfur content in the mixture, wt %
$w_{i,}$=Weight fraction of compound i in the mixture, wt %
$S_i$=Sulfur content in compound i, wt %

H) Crude or Petroleum Fraction Mercaptan Sulfur Content $MS = \Sigma w_{i,} \cdot MS_i$ Where,
MS=Mercaptan sulfur content in the mixture, wt %
$w_i$=Weight fraction of mercaptan compound i in the mixture, wt
$MS_i$=Sulfur content in mercaptan compound i, wt %

I) Crude or Petroleum Fraction Total Nitrogen Content $TN = \Sigma w_i \cdot N_i$ Where,
TN=Total nitrogen content in the mixture, wt %
$w_i$=Weight fraction of compound i in the mixture, wt %
$N_i$=Nitrogen content in compound i, wt %

J) Crude or Petroleum Fraction Basic Nitrogen Content $BN = \Sigma w_i \cdot BN_i$ Where,
BN=Basic nitrogen content in the mixture, wt %
$w_i$=Weight fraction of basic nitrogen containing compound i in the mixture, wt %
$BN_i$=Nitrogen content in basic nitrogen containing compound i, wt %

K) Crude or Petroleum Fraction Carbon Content $C = \Sigma w_i C_i$

Where,
C=Carbon content in the mixture, wt %
$w_i$=Weight fraction of compound i in the mixture, wt %
$C_i$=Carbon content in compound i, wt %

L) Crude or Petroleum Fraction Hydrogen Content $H = \Sigma w_i \cdot H_i$

Where,
H=Hydrogen content in the mixture, wt %
$w_i$=Weight fraction of compound i in the mixture, wt %
$H_i$=Hydrogen content in compound i, wt %

M) Crude or Petroleum Fraction C-to-H Ratio $$C\text{ to }H = \frac{C\ \%}{H\ \%}$$

Where,
C %=Carbon content in the mixture, wt %
H %=Hydrogen content in the mixture, wt %

Compound Selection and UI Segment Representation

Compounds in a library such as the MC library are selected to represent the assay data during the characterization process. Not all compounds available in the library are required to describe the properties for a given assay. The compound selection process depends on the types and qualities of data available. The primary method used in compound selection uses distributions of conceptual segments, which represent the compound classes (See classes shown in Table 1 of FIG. 19) to determine the probability of the compounds in a given class to exist in the crude or petroleum fraction. The conceptual segments were chosen to represent all compound classes and structures considered and are summarized in Table 4 of FIG. 22. Examples of these conceptual segments include total carbon number, one-branched methylene, two-branched methylene, naphthenic side ring, and aromatic side ring. Table 4 of FIG. 22 shows conceptual segment types and segment structures representing compound classes in Table 1 of FIG. 19. The distributions of these conceptual segments are used in the compound selection process.

Figure 3:
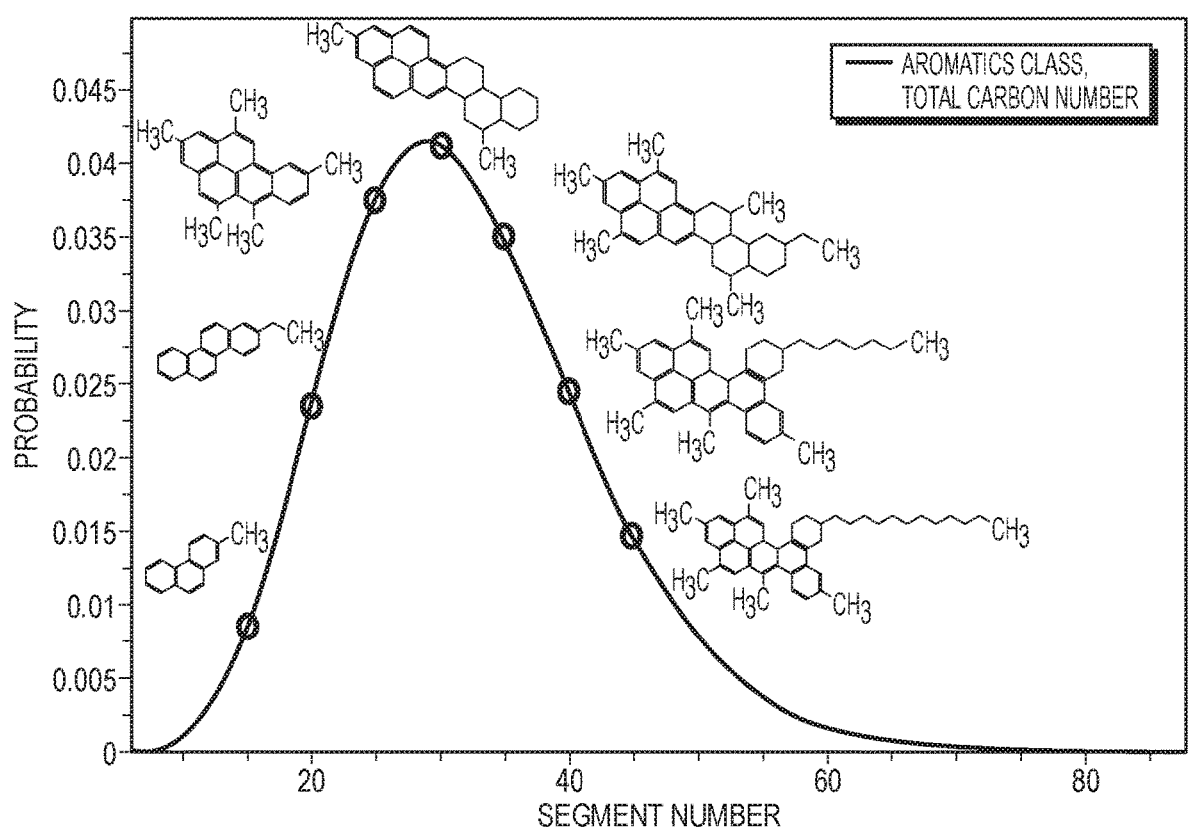
FIG. 3 shows an example probability distribution of the 'Total carbon number' segment type. Illustrated in the figure are the compounds with various carbon number selected at different segment numbers.

Segment distribution describes the probability of the segment type as a function of the segment number. The "Total Carbon Number" distribution is the probability of having compounds of 1, 2, 3, 4, . . . number of carbon atoms. As shown in FIG. 3, the probability of having a compound with a total carbon number of 30 is around 0.0413. This conceptual segment controls the carbon number in the compound, no other segments have any effect.

The 'One-branch methylene' and 'Two-branch methylene' segments controls the degree of paraffinic branching for isoparaffins.

Figure 4:
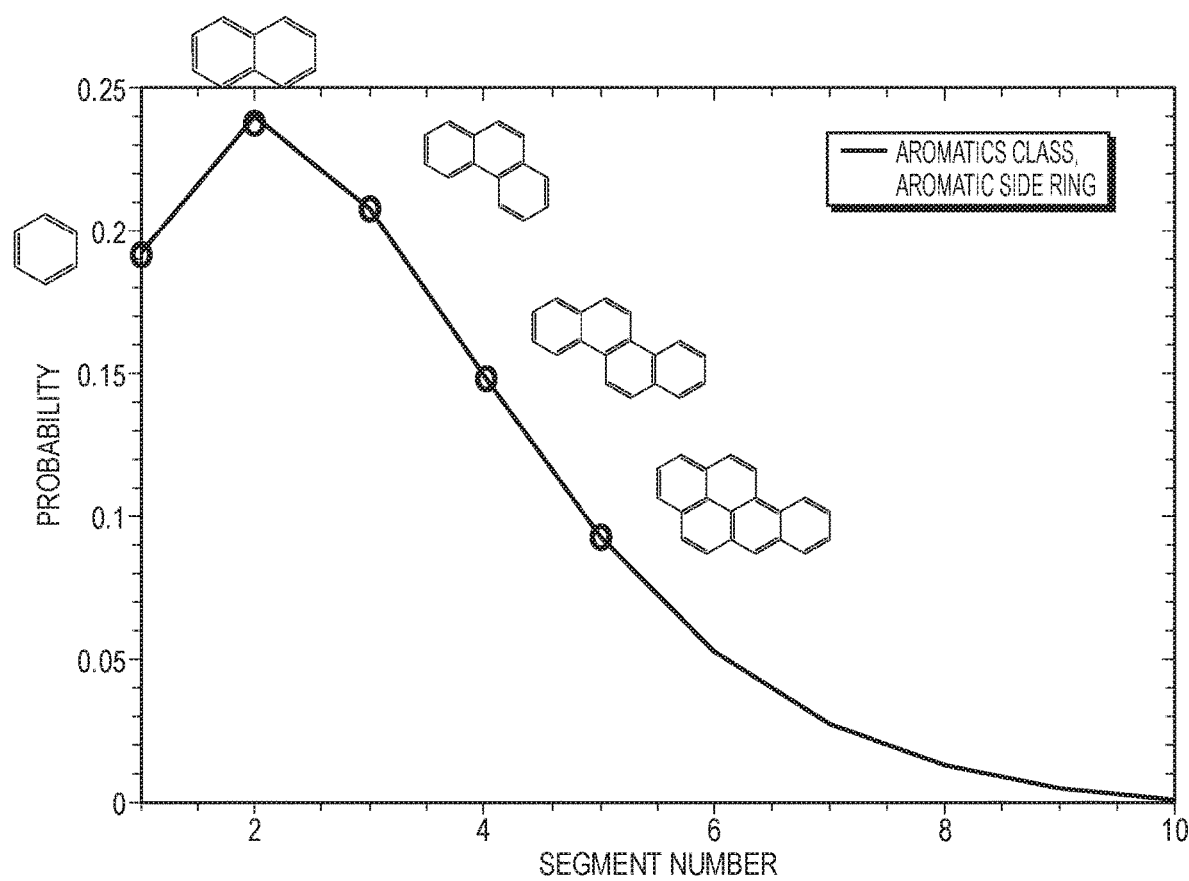
FIG. 4 shows an example probability distribution of the 'Aromatic side ring' segment type. Illustrated in the figure are the compounds with various aromatic rings selected at different segment numbers.
Figure 5:
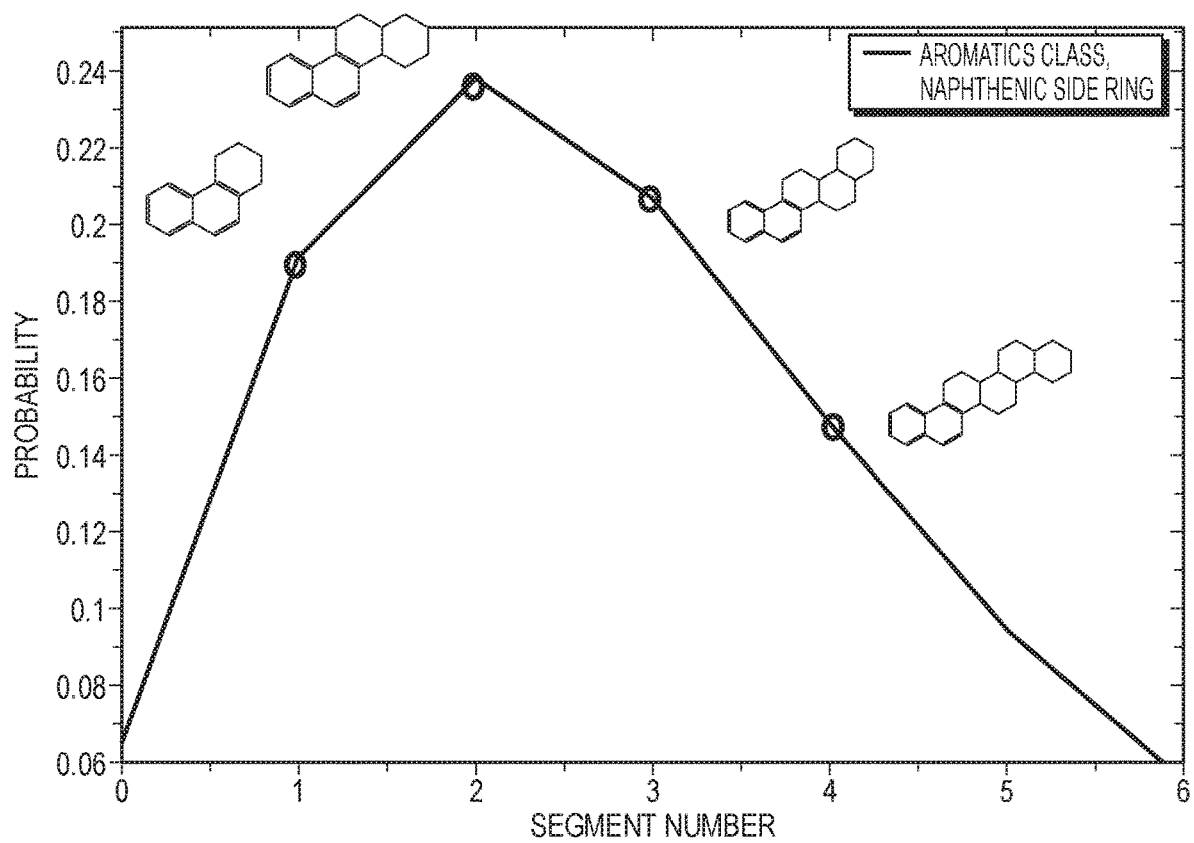
FIG. 5 shows an example probability distribution of the 'Naphthenic side ring' segment type. Illustrated in the figure are the compounds with various naphthenic rings selected at different segment numbers.

The 'Aromatic side ring' and 'Naphthenic side ring' segments control the ring count distribution. FIG. 4 and FIG. 5 show examples of distribution of aromatic and naphthenic side rings, respectively. Different segment numbers are included for illustrative purposes. A naphthenic side ring value of zero indicates that the compound has no naphthenic rings. A value of 1, indicates that the compound contains one naphthenic ring. Table 5 of FIG. 23 shows examples of compounds and the corresponding conceptual segments and values that are used in their selection process.

The probability of the conceptual segments are used to calculate the mole fractions of the selected compounds using the following equation:

$$y_i = \gamma_C^{class} \cdot p_{s1}(n_1) \cdot p_{s2}(n_2) \cdot p_{s3}(n_3) \cdot \ldots \cdot p_{sk}(n_k)$$

Where, $y_i$=Mole fraction of compound i belonging to class C $y_C^{class}$=Mole fraction of compound class C $n_{1, 2, \ldots, k}$=Segment number $p_{s1, s2, \ldots, sk}$=Probability at segment type s1, s2, ..., sk. These probabilities could be calculated from the probability distribution functions defined for the segments, such as gamma function, uniform function, or Aspen function.

A complete list of segments and sample compounds that can be selected by the segments are shown in Table 6 of FIG. 24. The remaining "Mole fraction of . . . " segments, which include: '6CR,' 'Paraffinic Sulfide,' 'SO2,' Thiophene, "NO2,' 'Neutral Nitrogen,' 'Basic Nitrogen Paraffinic Sulfide,' and 'Aromatic Acid,' alter the ratio of two subclasses between two shared class distributions. For example, the mole fraction of aromatic acid segment is used to determine or specify the proportion of aromatic acid vs. naphthenic acid in the oxygen-compound class. If experimental data is available that distinguishes between these two types of acids, the mole fraction can be set directly using the data. When data is not available, this variable can be arbitrarily set by the user or adjusted by regression.

An important concept of molecular characterization is called "molecular profile". A specific molecular profile is associated with a sample containing a crude oil or a petroleum fraction. The profile is used to represent the molecules within the library (e.g., the MC library) that are present in the sample containing the crude oil or petroleum fraction and their compositions. The profile consists of the following key information: Relative weight of each compound class (e.g., compound classes of Table 1 in FIG. 19), conceptual segment types of each class (e.g. the segments of Table 4 in FIG. 22), the segment distribution information for each segment, and viscosity parameters.

Each of the segment distributions is further described by the use of one of the following: uniform distribution, gamma distribution, and "Aspen" distribution. The uniform distribution produces a "constant" distribution. Gamma distribution function is commonly used because it contains two adjustable parameters that can be used to describe a wide range of distributions. The Aspen distribution represents the probability of a segment at discrete integer values of the segment number as derived from experiments.

Experimental Data Processing

Figure 6:
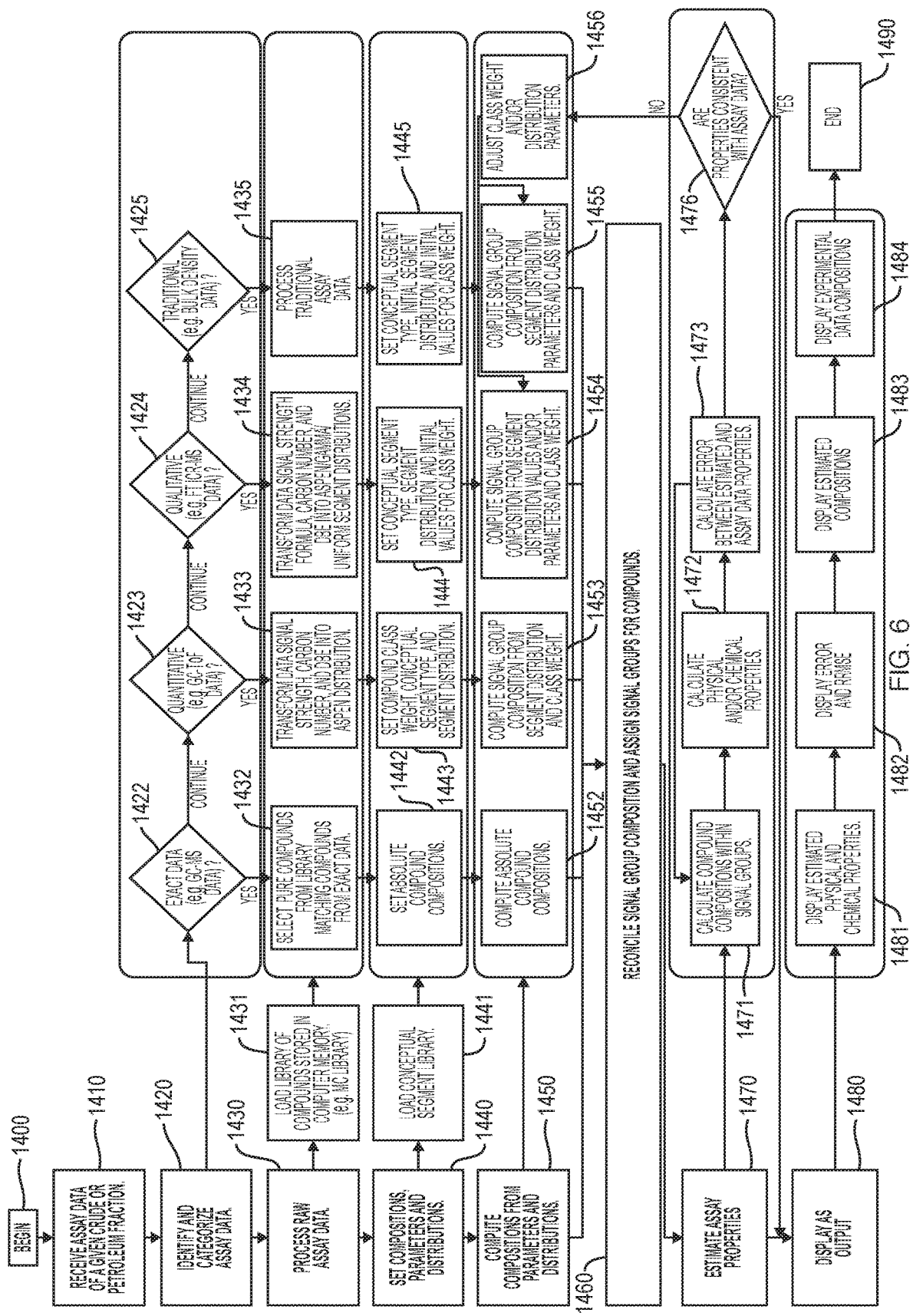
FIG. 6 is a flow diagram of the computer-implemented characterization method used to compute the chemical composition and estimated properties of a crude or petroleum fraction.

The methods of the present invention can use many types of experimental data as illustrated in FIG. 6.

The methods of the present invention can use traditional assay data.

Traditional assay data includes, but is not limited to, distillation curve data, density curve data, sulfur curve data, basic nitrogen curve data, total nitrogen curve data, carbon-to-hydrogen ratio curve data, total acid number curve data, PIONA content curve data, viscosity curve data, nickel content curve data, and vanadium content curve data.

The methods of the present invention can use gas chromatography and mass spectrometry data referred to herein as advanced analytical measurements or detailed molecular level data.

The assay data can include advanced analytical measurements from gas chromatography and mass spectrometry methods, including GC-MS, GC-ToF, and FT ICR-MS data.

GC-MS data identify compounds or lumps present in the sample and their compositions. Lumps are aggregates of many compounds that are structural isomers; they have the same chemical formula and belong to the same class, such as C6-isoparaffins, C7-naphthenes, or 8-carbon-aromatics. Since the compound or lump identity and composition are known quantitatively, this type of data is considered quantitative. This type of data is also referred to in subsequent sections as "Exact" data.

GC-ToF data is presented in the form of signal strength as a function of carbon number, molecular class, and double bond equivalent (DBE). The signal strength is transformed into mole fraction in the data processing step of the algorithm. GC-ToF data is considered quantitative, therefore, the weight percent of each molecule class can also be determined.

Figure 7:
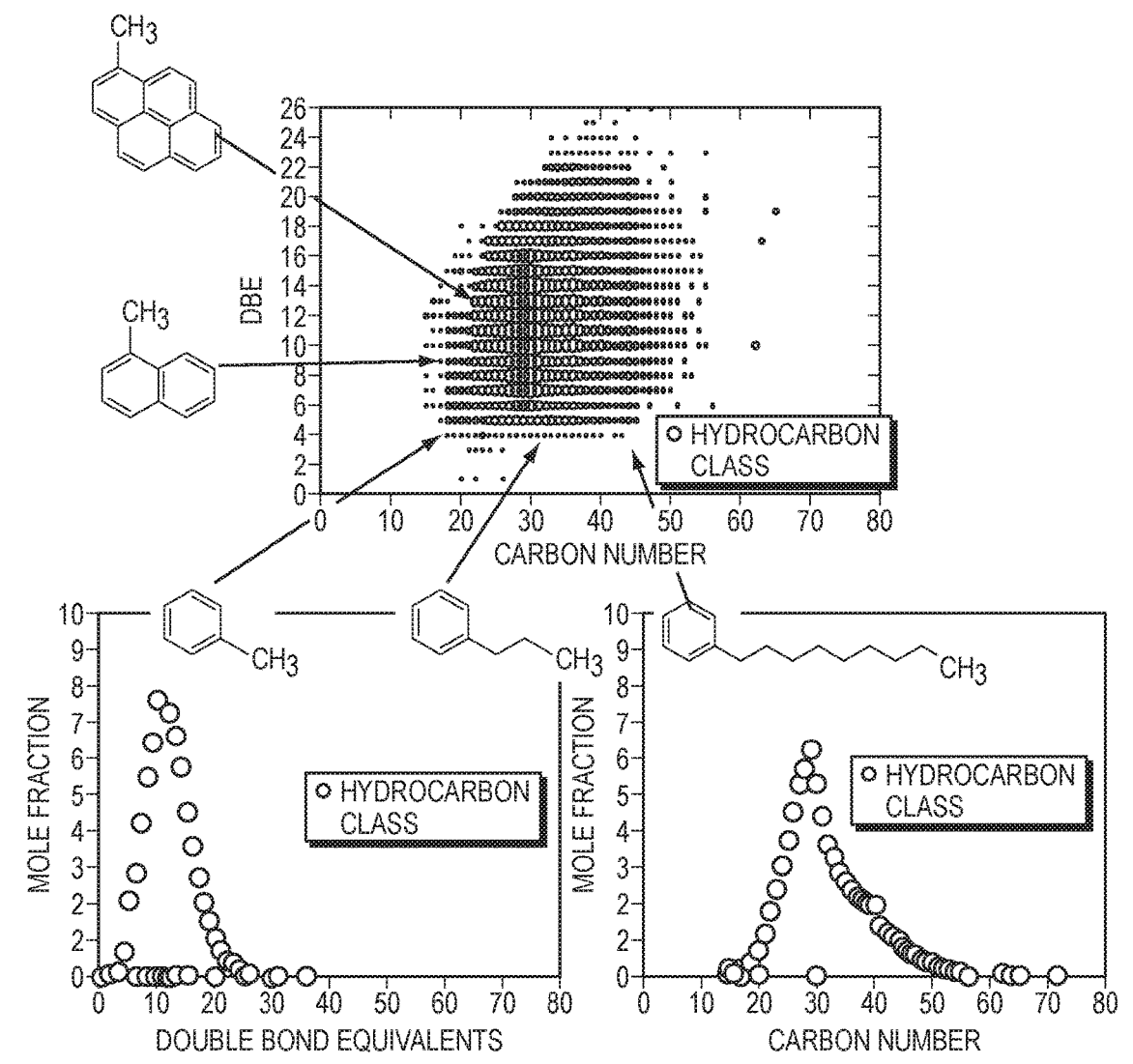
FIG. 7 shows experimental data from APPI FT ICR-MS. It creates a 2D signal distribution as a function of Carbon Number vs. Double Bond Equivalents for the Aromatic class. The two distributions are further abstracted into a separate distribution of Carbon Number and a distribution of DBE for the Aromatic class. The molecule pictures point to one potential isomer of many possible molecules contained within the data signal.

FT ICR-MS data (e.g. APPI, ESI−, ESI+) is presented in the form of signal strength as a function of carbon number, Kendrick molecular weight, suggested molecular formula, molecular class, and double bond equivalent. The signal strength data is transformed into mole fraction in the data processing step of the algorithm. FT ICR-MS data are currently qualitative, therefore, the class weight and composition cannot be set directly. However, their relative distributions are maintained by the algorithm. An example of such data can be seen in FIG. 7, where the APPI FT ICR-MS measurement defines the carbon number distribution and DBE distribution, essentially a distribution of chemical formulas, for the aromatic hydrocarbon class. The FT ICR-MS data provides key information on the relative compositions within this class of compounds.

The type of data available depend on the detection limits of the instrument and experimental procedure, which functionally, limits the data type to a specific boiling range. Currently, GC-MS measurements are applicable to samples that boil below 200° C. Currently, GC-ToF measurements have a suitable detection range for fractions that boil between 160° C.-350° C. Currently, FT ICR-MS measurements are applicable for heavy fractions of the crude, such as the residue (>350° C.). Depending on the procedure, current FT ICR-MS measurements can be applied to samples that boil below 350° C. as well. See FIG. 8.

The methods of the present invention can process one or more of the data types simultaneously. As shown in FIG. 8, a typical crude oil sample can be fractionated into different fractions. GC-MS, GC-ToF, FT ICR-MS, or traditional assay measurements can be performed on the same fraction. Another example, is for a sample that is a light petroleum fraction (e.g. one with a boiling range below 200° C.). In this case, GC-MS data is typically measured.

Figure 9:
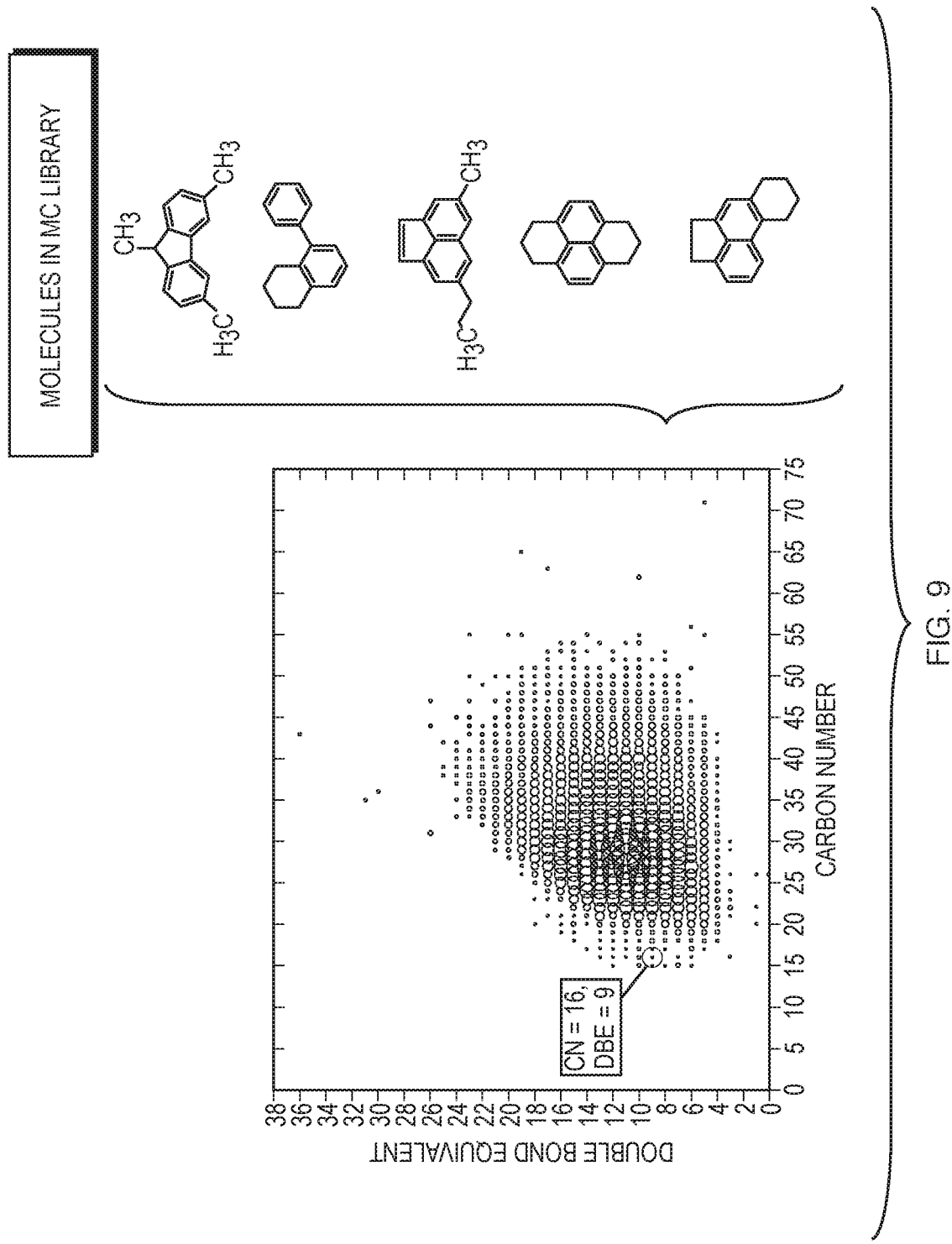
FIG. 9 shows isomers in the MC library that can be used to represent a data signal for a hydrocarbon class with CN=16 and DBE=9.

Some current measurement techniques, such as GC-ToF and FT ICR-MS cannot identify the exact molecules that are present in a data signal. That is, they cannot determine the compositions and identity of the isomers in the data signal. FIG. 9 shows an example of possible isomers that may exist in a data signal for a hydrocarbon class with CN=16 and DBE=9. In reality, with CN of 16, the actual number of possible isomers is significantly larger.

Data that can be employed for the present invention are categorized by considering the following 5 pieces of information or factors:

1. Composition of compounds (Absolute compositions vs. relative compositions)
2. Isomer identification (Exact isomer compounds identity vs. Structural Formula)
3. Carbon number
4. Double Bond Equivalent 5. Heteroatom content Data that does not contain some of the information is considered to have different levels of ambiguities. Measurements that can resolve this ambiguity take precedence over those that do not.

a) 'Exact' information determines all 5 of these factors, leaving no ambiguity to the molecules present and their compositions. Certain GC techniques, such as GC-MS are capable of determining these 5 pieces of information.

b) 'Exact' lump data can determine 4 of these factors. For this type of data, isomer compounds in the lump are not identified, while carbon number, DBE, composition and heteroatom content are defined. Therefore, the isomer constituent of the lump is the unknown (ambiguity) of this data type.

c) 'Quantitative' information can determine 4 of these factors. In the case of GC-ToF measurements, the isomer structure is often not identified, while the carbon number, DBE, composition, and heteroatom content are defined for each data signal. Therefore, the isomer constituent of the data signal is the unknown (ambiguity) of this data type.

d) 'Qualitative' information can determine 3 of these factors. One example is FT ICR-MS techniques (APPI, ESI+, ESI−), where the absolute composition and isomer types are not determined, but the carbon number, DBE, and heteroatom content are known for each data signal. For this type of data, the isomer constituent and composition of the data signal are the unknowns.

e) 'Traditional Assay Data' information may have only one of these factors defined. For example, using sulfur and nitrogen content data, heteroatom content can be inferred.

Signal Group

Due to ambiguity of some types of experimental data as described above, a data signal cannot be mapped directly to one or more specific compounds in the MC library. According to embodiments of the invention, a signal group is created to facilitate modeling of the data signal, especially those that have ambiguity. A signal group is a modeling construct, which comprises one or more model compounds that have been selected from the model compound library that meet the criteria set based on the type and quality of the assay data being processed and the conceptual segment probability distribution function being used. For exact data, such as GC-MS data that contain exact compound identity, a signal group comprises a compound selected from the model compound library, the compound having the same identity. For exact data, such as GC-MS data that is a lump, a signal group comprises a plurality of model compounds having the same class and carbon number. For quantitative molecular level data, such as GC-ToF data, a signal group comprises a plurality of model compounds having the same class, same carbon number and same double bond equivalent. For qualitative molecular-level data, such as FT ICR-MS data, a signal group comprises a plurality of model compounds having the same class, same carbon number and same double bond equivalent when the Aspen distribution is used for at least part of the data. For this type of data, a signal group also comprises a plurality of the model compounds having the same class, same carbon number, same one-branch methylene number, same two-branch methylene number, same aromatic side ring number, and same naphthenic side ring number when the Gamma distribution or uniform distribution is used to represent at least part of the data. For traditional assay data, a signal group comprises a plurality of the model compounds having the same class, same carbon number, same one-branch methylene number, same two-branch methylene number, same aromatic side ring number, and same naphthenic side ring number. When assigning one or more model compounds to a signal group, exact data has higher priority than exact lump data, exact lump data has higher priority than quantitative molecular-level assay data, quantitative molecular-level data has higher priority than qualitative molecular-level assay data, and qualitative molecular-level assay data has higher priority than traditional assay data. When assay data of differing priority exists which each would allow assigning a model compound to a signal group, assay data with highest priority is used to assign the model compound to the signal group.

Physical properties of a signal group are determined from the properties of the constituent compounds. Chemical formula, CN, and elemental contents of the signal group are the same as those for one of the constituent compound. Vapor pressure, normal boiling temperature, liquid density and other properties are calculated from the composition of the constituent compounds and their properties.

Signal Group and Molecule Selections Using Probability Distributions

An algorithm is developed to determine the probabilities of conceptual segments in Table 4 of FIG. 22 and relative class weight of constituent classes, which are then used to create signal groups and calculate compositions of the signal groups.

Figure 10A:
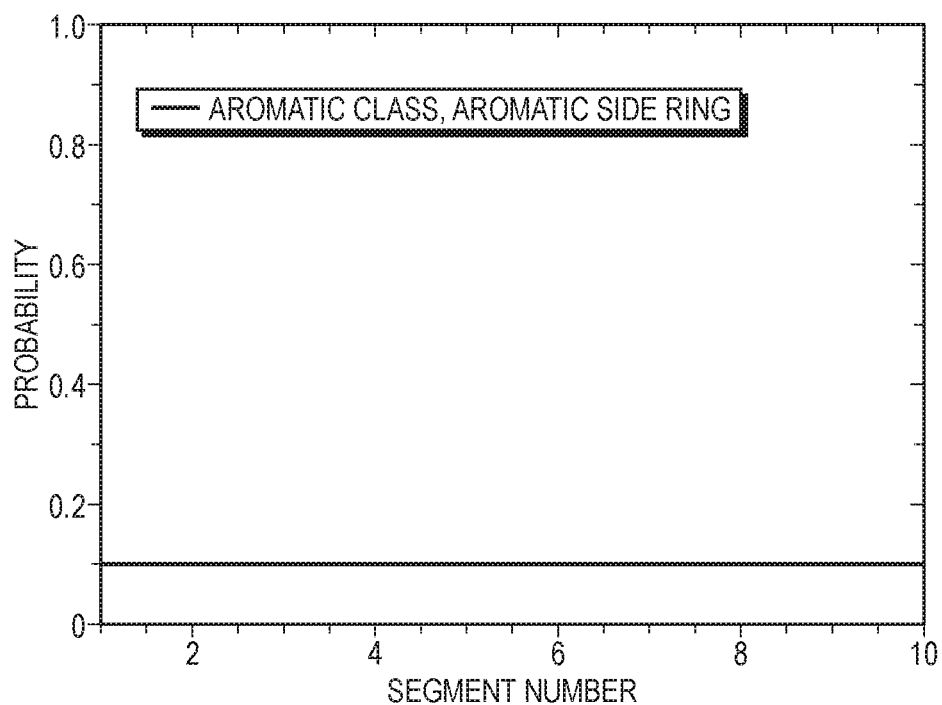
FIG. 10A provides a plot of an even probability distribution of molecules, that is, a constant probability over the segment number range.

The calculation option 'Uniform' selects an even probability distribution of the conceptual segment type as a function of segment number. FIG. 10A shows an example of a distribution resulting from the use of the 'Uniform' function. The uniform distribution function is used to process traditional assay data or to fill gaps in qualitative molecular level data.

$$p(n) = \frac{1}{n_{tot}}$$

Where:
p(n)=Probability at segment number n
n=Segment number
$n_{tot}$=Total number of segments in the distribution The calculation option 'Gamma' selects a gamma probability distribution of the conceptual segment type as a function of segment number. The underlying equation can be represented by:

$$p(n) = \frac{(n-L)^{\alpha-1} e^{-\frac{n-L}{\beta}}}{\beta^\alpha \cdot \Gamma(\alpha)}$$

Figure 10B:
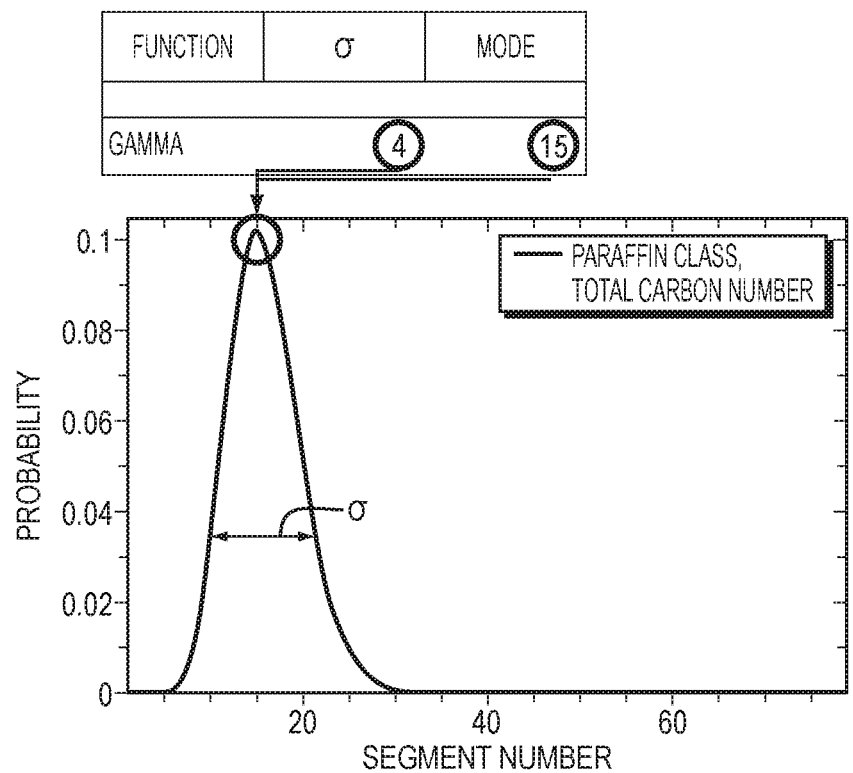
FIG. 10B provides a plot of a gamma probability distribution of molecules.

Where:
p(n)=Probability at segment number n
n=Segment number
L=Starting location of the probability function
α=Shape factor parameter
β=Scale parameter
Γ=Gamma function This equation is made orthogonal in the user interface, making it a function of Mode and standard deviation, σ. An example of a gamma distribution function with mode and σ parameters specified can be found in FIG. 10B. The gamma distribution function is used to process traditional assay data or to fill gaps in qualitative molecular level data. The mode and standard deviation, σ, parameters are referred to herein as the segment distribution parameters.

Figure 10C:
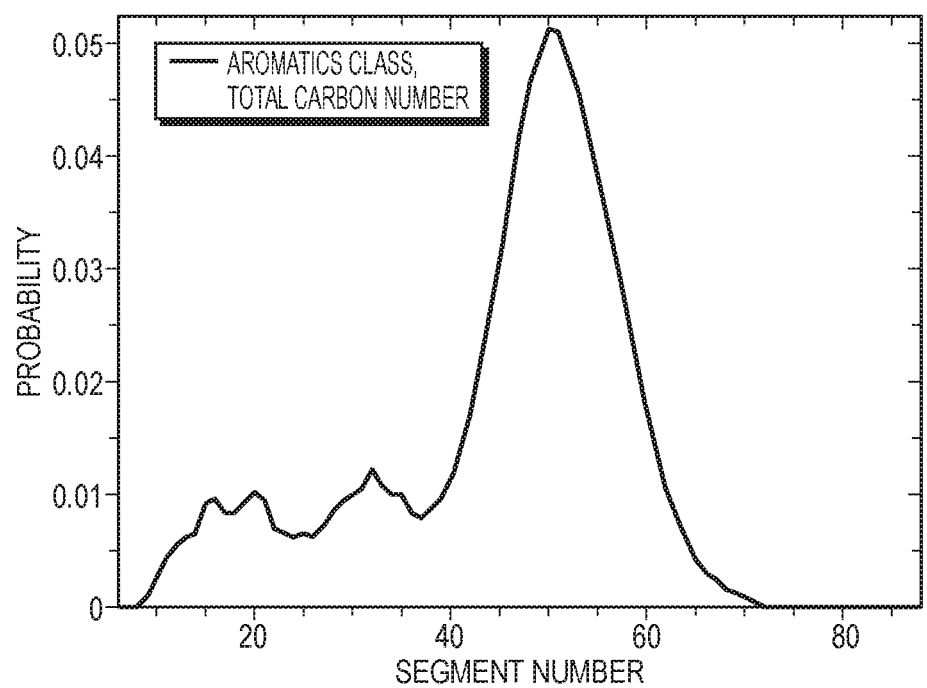
FIG. 10C provides a plot of a probability distribution of molecules set by detailed experimental data, here, for aromatics [HC] total carbon number.
Figure 11A:
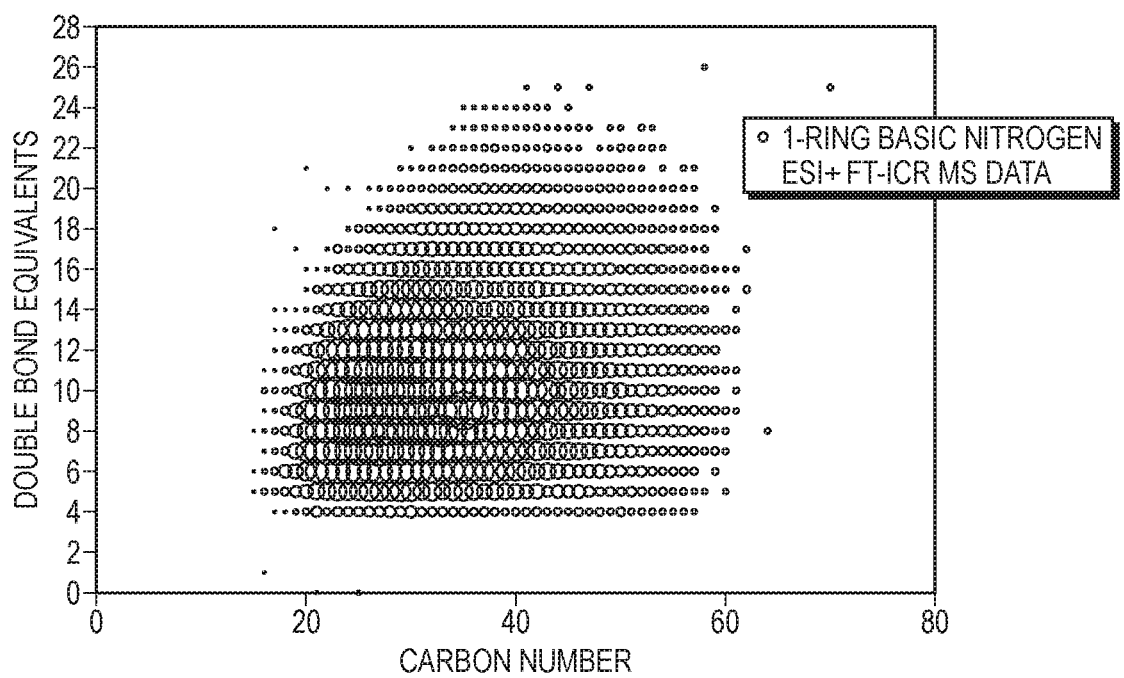
FIG. 11A is a plot of experimental data of double bond equivalents vs. carbon number obtained from one-ring basic nitrogen class measurements using ESI+FT ICR-MS.
Figure 11B:
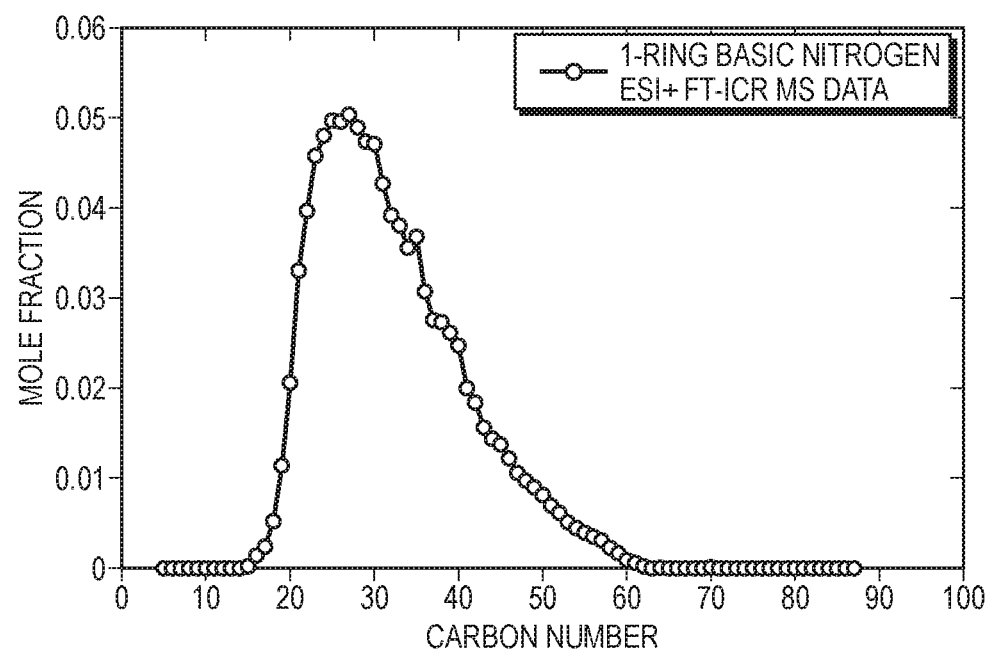
FIG. 11B is a composite distribution curve showing mole fraction vs. carbon number, which is generated from the data of FIG. 11A.
Figure 12:
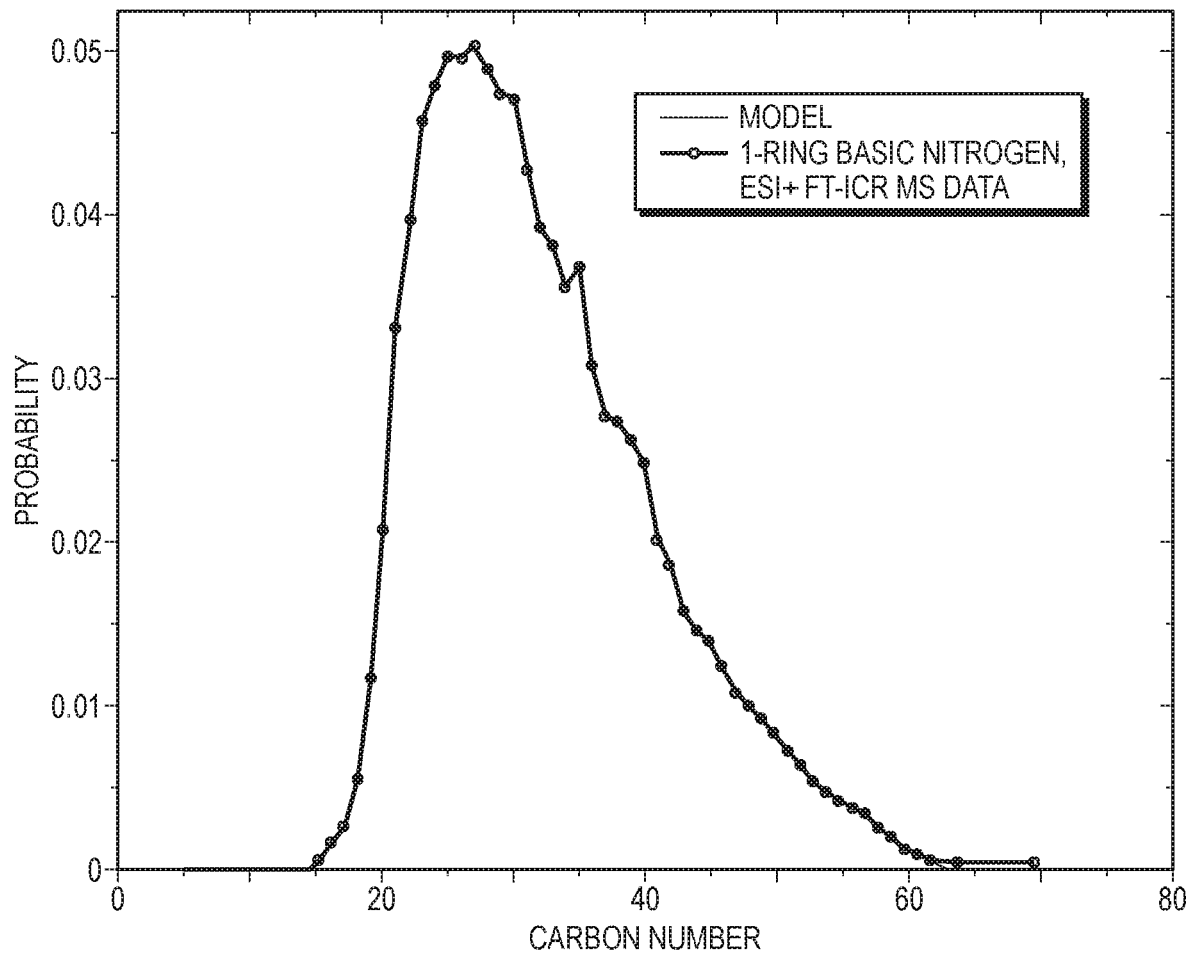
FIG. 12 is a graph of probability vs. segment number, where the segment type is basic nitrogen. The graph is obtained by methods described herein.

The calculation option 'Aspen' selects a probability distribution of the conceptual segment type that transforms quantitative and qualitative molecular level data such as GC FI-ToF and APPI/ESI+/ESI– FT ICR-MS data into a probability distribution values at integer values of the segment numbers. FIG. 10C shows an example of a distribution using the 'Aspen' function. FIG. 11A shows experimental data from ESI+FT ICR-MS in the form of a Carbon Number, DBE, and signal strength plot. FIG. 11B shows this same experimental data from ESI+FT ICR-MS in the form of a carbon number distribution. The algorithm, when this type of data is available, transforms the experimental signal strengths from the measurements into a normalized distribution to match the experimental data. The resulting 'Aspen' function used to model the carbon number distribution can be seen in FIG. 12. The Aspen distribution function is described as follows:

$$p(n) = \frac{\text{Intensity}_n}{\Sigma \text{Intensity}}$$

Where:
p(n)=Probability at segment number n
$\text{Intensity}_n$=Experimental data signal strength at n
ΣIntensity=The summation of signal strength over all measurements The value of the probability of the Aspen distribution is referred to herein as the segment distribution value.

Figure 13:
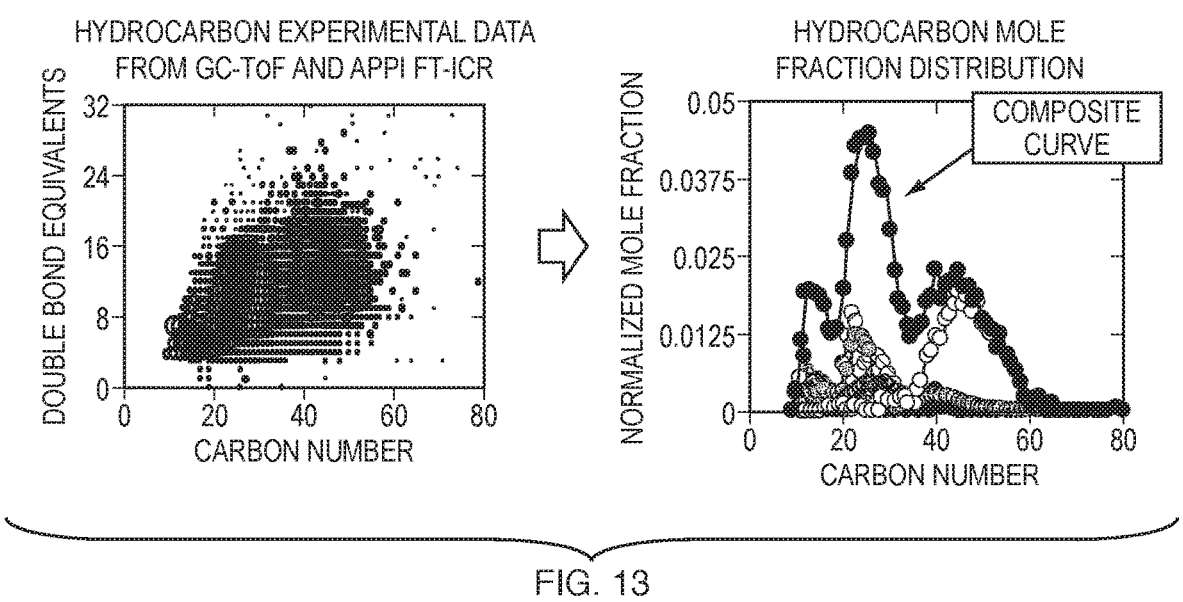
FIG. 13 illustrates converting a plot of DBE vs. carbon number to a plot of normalized mole fraction vs. carbon number.

The algorithm determines probabilities of the Aspen distribution function from quantitative or qualitative molecular level data by constructing a composite of the constituent cuts data if any in the range of interest. FIG. 13 on the left shows the experimental data, while FIG. 13 on the right shows the processed data using the 'Aspen' function.

The algorithm determines the probabilities by combining the Aspen distribution with the gamma distribution.

The algorithm combines GC-MS data with the Aspen and gamma distributions to determine the compositions of signal groups.

Figure 14:
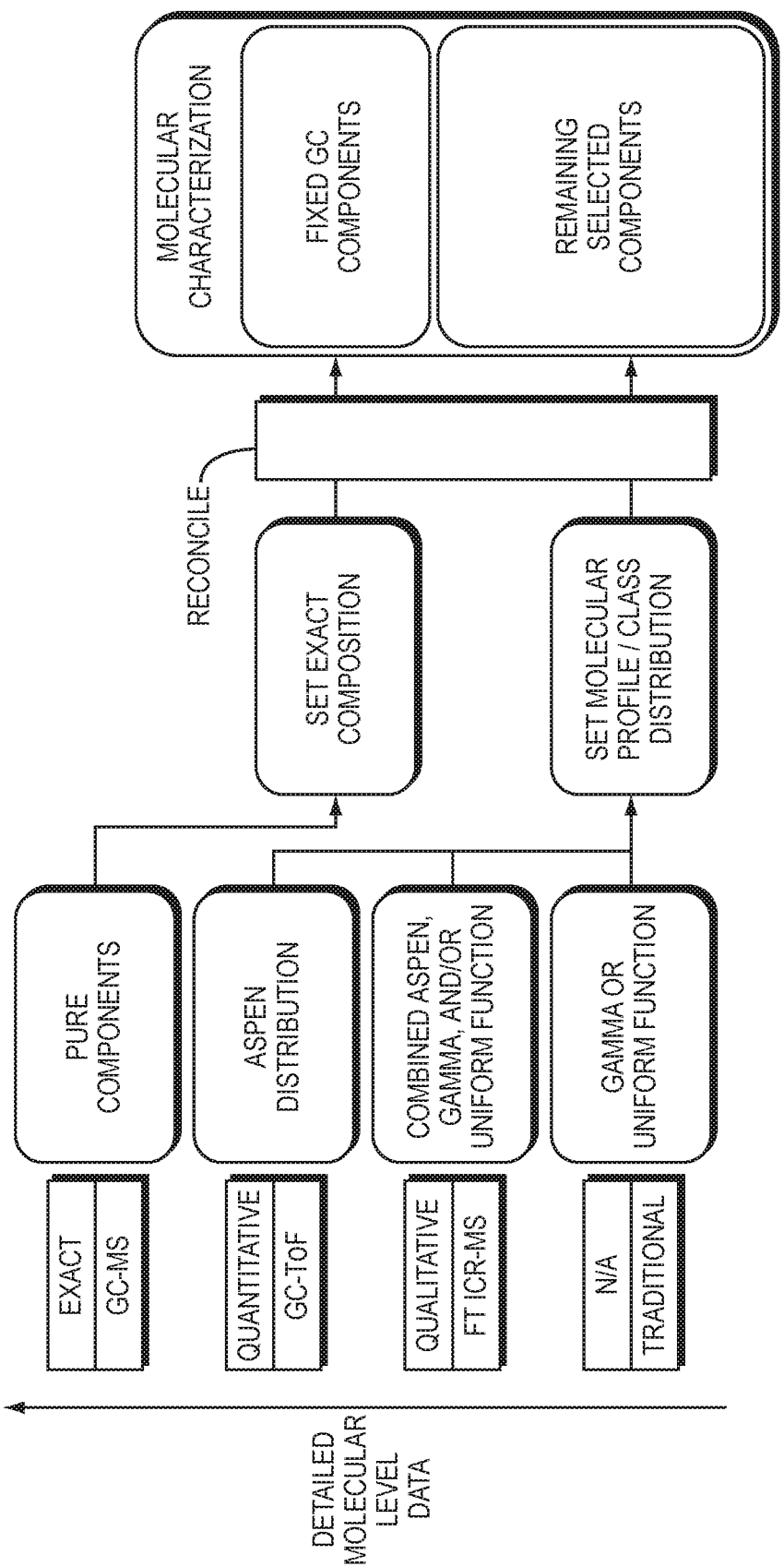
FIG. 14 illustrates the sequence and priority of the calculations determined by the type and quality of the data. Data obtained using instruments and techniques that provide higher precision and accuracy with less ambiguity in the identification of molecules represented in measurement take precedence over less accurate or more ambiguous data when they are used simultaneously.

The algorithm creates the molecular characterization of the sample by use of the available data, based on the data type and level of molecular details of the data, as shown in FIG. 14 and described in the EXPERIMENTAL DATA PROCESSING section. Data that contains less ambiguity takes precedence over those that have more.

Figure 15:
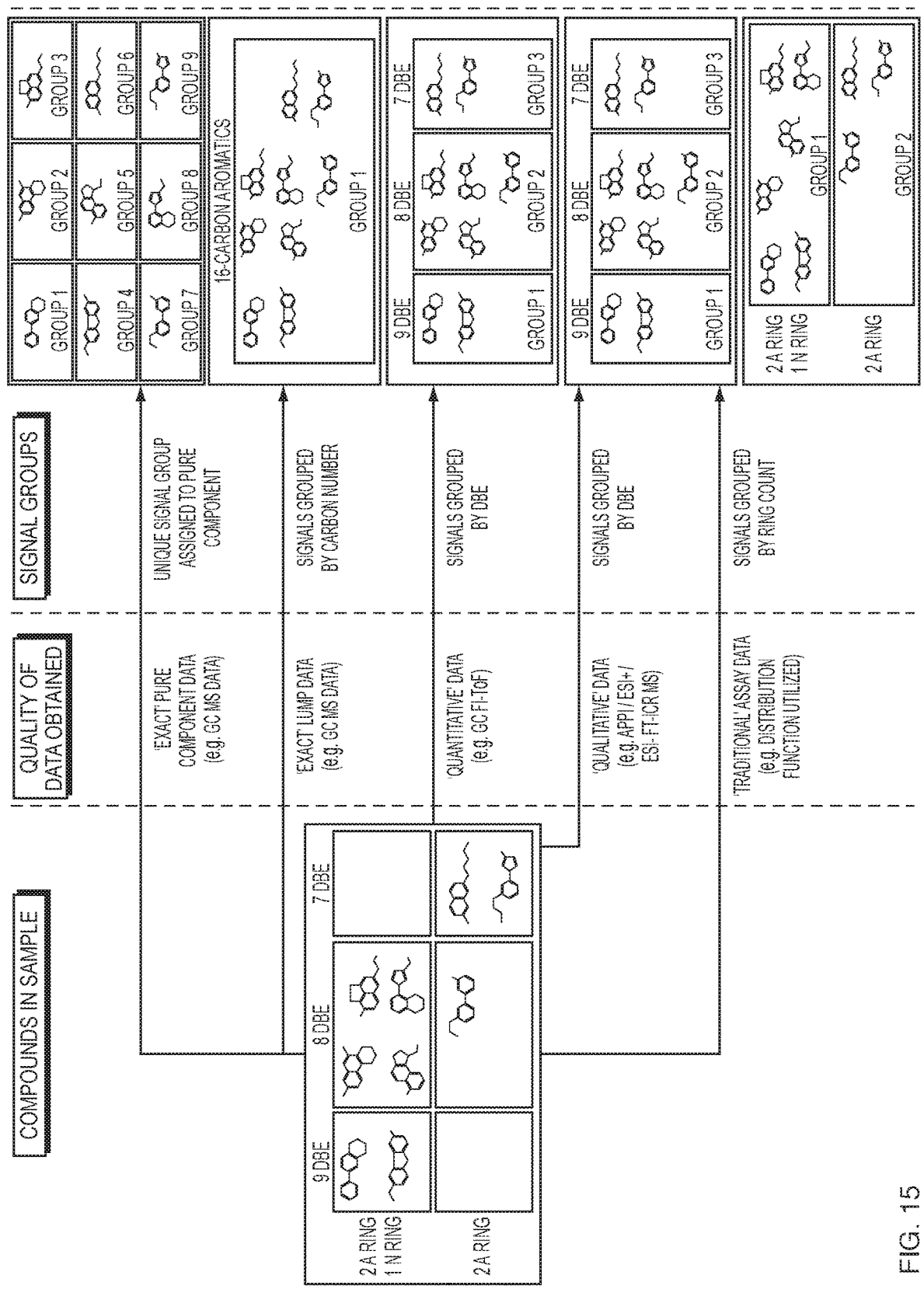
FIG. 15 illustrates data signal processing heuristics for a hypothetical sample that contains nine hydrocarbon compounds with CN=16, different DBEs and different numbers of aromatic and naphthenic rings.

FIG. 15 illustrates data signal processing heuristics for a hypothetical sample that contains nine hydrocarbon compounds with CN=16. By using different measurement techniques, which yield different qualities for the obtained data, the resultant signal groups determined by the present algorithm are different.

a) Using measurement technique that provides 'Exact' pure component data, where the composition and identities of the nine compounds were determined, each compound is treated as a signal group for processing purpose with composition of the signal group fixed to the measurement composition value.

b) Using measurement technique that provides "Exact" component lump data, where only the composition of the C16 lump is known, a signal group is created that comprises the nine isomer compounds. The composition of the signal group is fixed to the measurement composition value of the lump. The compositions of the 9 isomer compounds within the signal group are initially set to the measured composition of the lump divided by 9.

c) Using measurement technique that provides 'Quantitative" data that include the carbon number, DBE, composition, and heteroatom content, three signal groups are created. Each signal group contains compounds with 9 DBE, 8 DBE and 7 DBE, respectively. The composition of each signal group is fixed to the measured signal strength (i.e., measured composition) of the data signal of the respective CN=16 and DBE value. The compositions of the isomer compounds within each signal group are initially set to the composition of the data signal divided by the number of constituent isomer compounds (2, 5, and 2 for the first, second, and third signal groups, respectively).

d) Using measurement technique that provides 'Qualitative" data that include the carbon number, DBE, relative composition, and heteroatom content, three signal groups are created. Each signal group contains compounds with 9 DBE, 8 DBE and 7 DBE, respectively. Since exact composition of the data signal is not available, the composition of each signal group cannot be fixed, but will be determined by material balance and data regression as part of the algorithm depicted in FIG. 6.

e) Using measurement technique that provides 'Traditional Assay Data', gamma distribution function is utilized to generate two signal groups characterized by ring count. The first signal group contains compounds having CN=16, two aromatic rings and one naphthenic ring. The second signal group contains compounds having CN=16 and two aromatic rings. The composition of the signal groups will be determined by material balance and regression of the segment distribution parameters as depicted in FIG. 6.

The algorithm creates the molecular characterization of the sample by reconciling the signal groups composition determined from different data types based on the quality/certainty of the data and yields of the constituent fraction of the sample. As shown in FIGS. 6 and 8, in the reconcile step the 'Exact' data from GC-MS holds priority over 'Quantitative' data from GC-ToF in the 160° C.-200° C. boiling range. GC-ToF holds the highest priority in the 200° C.-350° C. range, which can be supplemented by 'Qualitative' FT ICR-MS data and traditional assay data. 'Qualitative' FT ICR-MS data in the >350° C. range takes precedence, as there is no other advanced analytical data, and can be supplemented by 'Traditional' assay data. Finally, the sample composition (of a crude or petroleum fraction) is normalized to 100%.

GC-ToF and FT ICR-MS data for petroleum fractions within an assay are weighted proportionally to their corresponding yield (by volume or weight).

Figure 16:
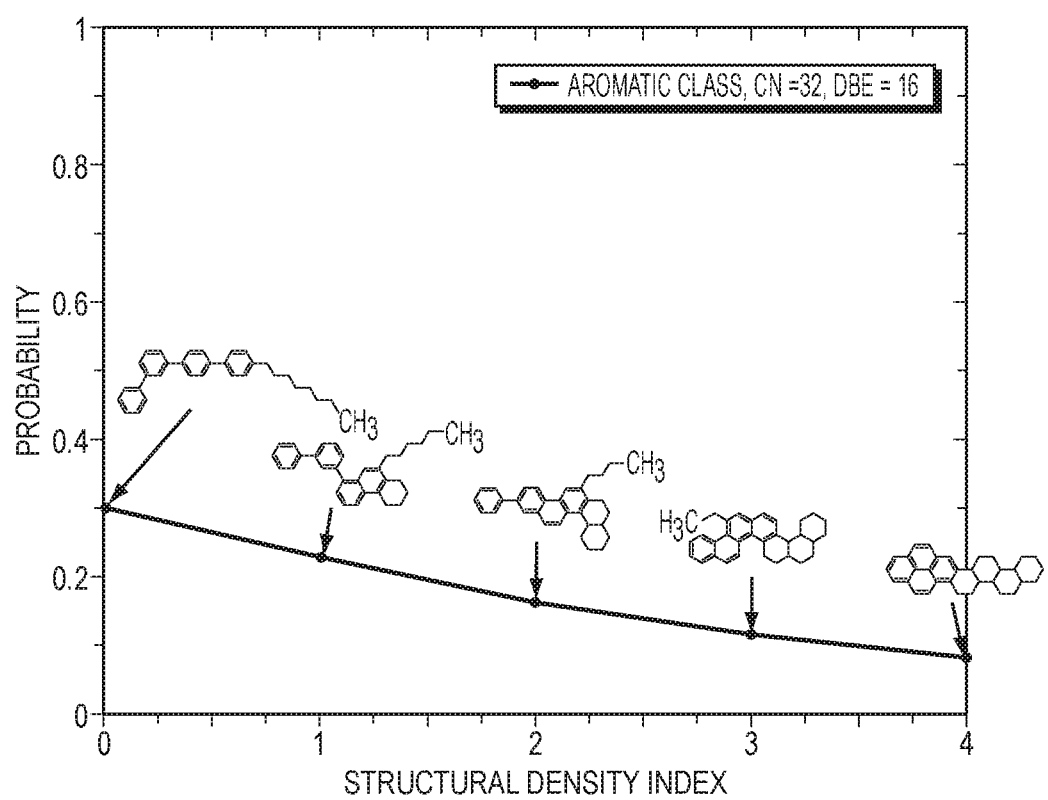
FIG. 16 shows an example probability distribution of the structural density index for aromatic class compounds with CN=32 and DBE=16.

Once the signal groups have been determined, the algorithm calculates the compositions of the individual constituent compounds within the signal groups. For each signal group, the underlying compounds are assigned a characteristic value based on its structure, herein referred to as the structural density index. What is often the case is that the structural density index, when ordered, also order the compounds from lowest boiling temperature and density to highest boiling temperature and density. The structural density index is represented using a gamma distribution function as shown in FIG. 16. One distribution function can be used to represent all compounds in all the signal groups of the sample or a plurality of distribution functions can be used, one representing compounds in the signal groups within a cut (fraction) of the sample.

To calculate the compositions of the constituent compounds within a signal group, for a given compound, it's assigned structural density index value is used to determine the probability value using a distribution function and parameters, as illustrated in FIG. 16 and tabulated in Table 7 of FIG. 25. The structural density probability distribution value for each compound is normalized, then scaled by the signal group's composition, resulting in a set of compositions for each compound in the signal group.

$$x_c = \frac{p(c)}{\sum_p p} * x_{Signal\ Group}$$

where:
  $x_c$=Composition (mole fraction) of compound c in the signal group
  p(c)=Structural density index probability value of compound c.
  $x_{Signal\ Group}$=Composition (mole fraction) of signal group The algorithm maintains a constant composition for the signal group. The resulting compound compositions, when summed within their respective signal group, equals the total composition of the signal group set by the reconcile signal group composition step.

$$x_{Signal\ Group} = \sum_c x_c$$

Table 7 of FIG. 25 shows a hypothetical calculation of individual compound compositions within signal groups using a distribution function shown in FIG. 16. Annotation in FIG. 16 shows the five compounds assigned to the second signal group in Table 7 of FIG. 25.

The algorithm may skip this step, provided that analytical techniques are capable of producing 'Exact' pure component identity and compositions for the entire sample because, in this case, the compositions of all the components within all the signal groups are known from measurements.

Objective Function

In certain embodiments, the experimental data are collected and used in regression procedure to identify the "molecular profile" for the crude or petroleum fraction. The regression procedure minimizes the objective function residual root-mean-square error (RRMSE) defined below using a non-linear least squares algorithm:

$$RRMSE = \sqrt{\frac{\sum_{i=1}^{k}\sum_{j=1}^{m}\left(\frac{Z_{ij} - ZM_{ij}}{\sigma_{ij}}\right)^2}{k-n}}$$

Where,
ZM=Measured (experimental) physical and chemical properties, see Experimental Data Processing section.
Z=Calculated value
σ=Standard deviation
i=Data point number
k=Total number of data points
j=Measured variable for a data point (such as cut yield, density, sulfur content, etc.)
m=Number of measured variables for a data point
n=Total number of adjustable parameters The adjustable parameters can be the mode and standard deviation, a, of the gamma distribution functions for the selected conceptual segments. The adjustable parameters can also include the mode and standard deviation a, of the structural density index gamma distribution functions that are used in the calculation of compositions of constituent compounds within signal groups.

Computer Implementation

Figure 17:
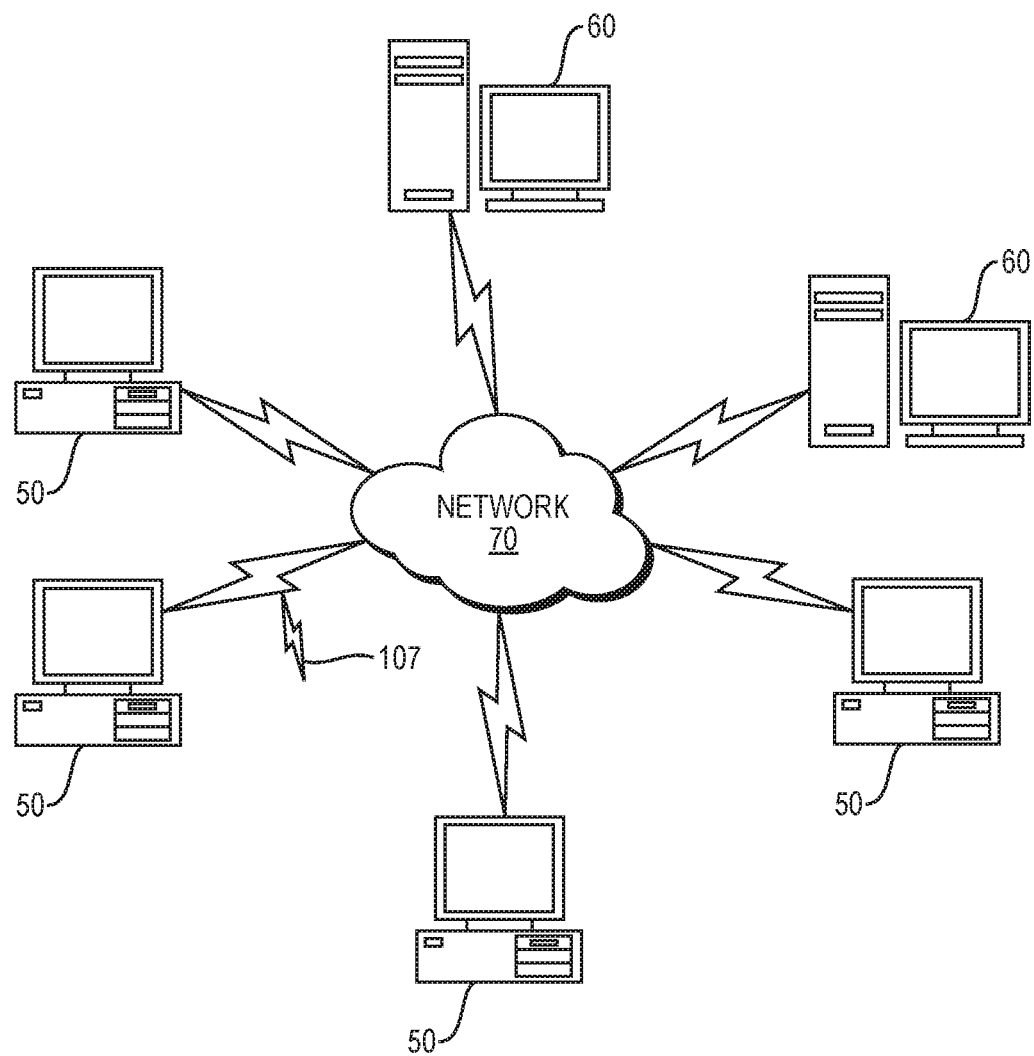
FIG. 17 illustrates a computer network or similar digital processing environment in which the present invention may be implemented.

FIG. 17 illustrates a computer network or similar digital processing environment in which the present invention may be implemented.

Client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 18:
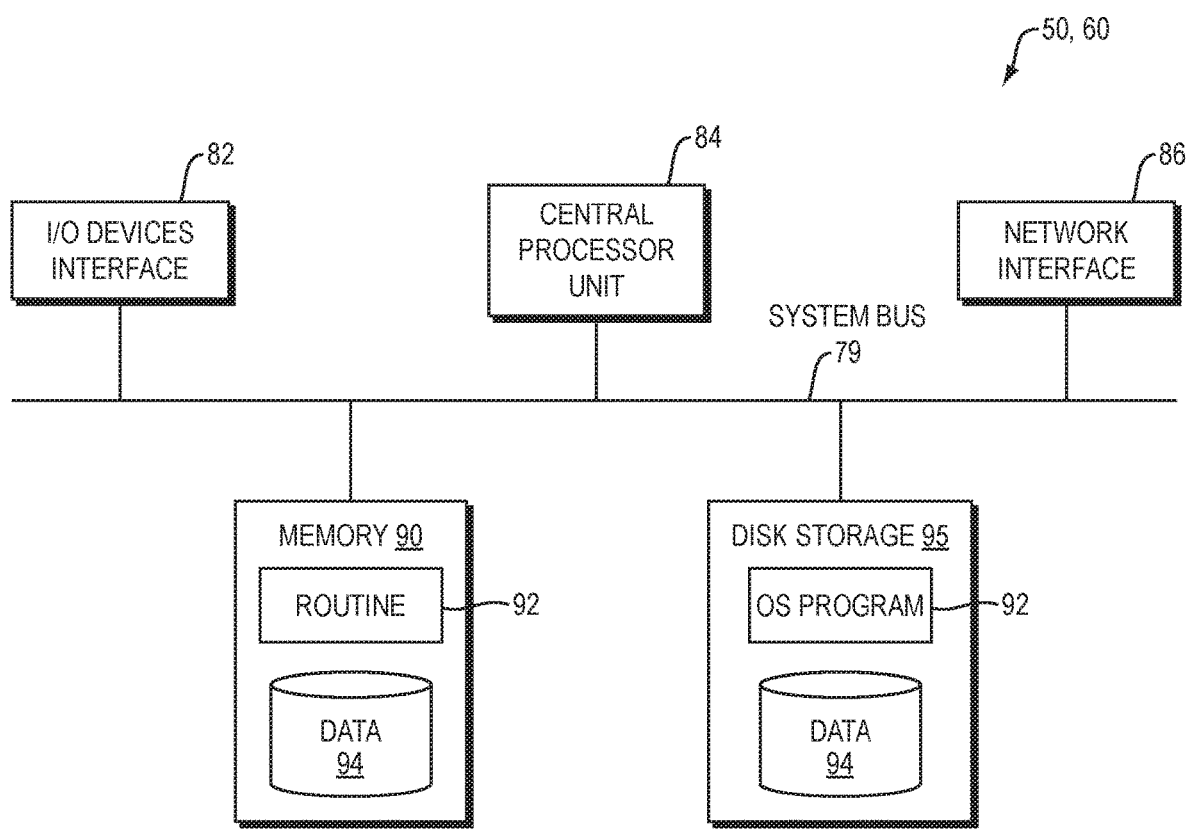
FIG. 18 is a diagram of the internal structure of a computer (e.g., client processor/device 50 or server computers 60) in the computer system of FIG. 17.

FIG. 18 is a diagram of the internal structure of a computer (e.g., client processor/device 50 or server computers 60) in the computer system of FIG. 17. Each computer 50, 60 contains system bus 79, where a bus is a set of hardware lines used for data transfer among the compounds of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 17). Memory 90 provides volatile storage for computer software instructions 92 and data 94 used to implement an embodiment of the present invention (e.g., virtual assay engine, crude oil assay modeler, and supporting code 700 detailed above and below). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

FIG. 6 is a flow diagram (processor routine) 1400 of an example embodiment of a computer-implemented method of characterizing chemical composition of a sample containing crude oil or a petroleum fraction.

At 1410, the computer system 50, 60 or processor receives assay data including one or more types of molecular-level gas chromatography and mass spectrometry data, and traditional assay data of the given sample containing a crude oil or a petroleum fraction.

At 1420, the computer system 50, 60 or processor processes, identifies and categorizes the assay data into exact data (e.g., GC-MS data), molecular-level quantitative data (e.g., GC-ToF data), molecular-level qualitative data (e.g., FT ICR-MS data), and traditional assay data and process each type of data in turn.

At 1422, the computer system 50, 60 or processor determines if the assay data comprises exact data, such as GC-MS data. If such data exists, the system proceeds to process the data at step 1432. If exact data is not available, the system proceeds to the next data type at 1423.

At 1423, the computer system 50, 60 or processor determines if the assay data comprises molecular-level quantitative data, such as GC-ToF data. If such data exists, the system proceeds to process the data at step 1433. If quantitative data is not available, the system proceeds to the next data type at 1424.

At 1424, the computer system 50, 60 or processor determines if the assay data comprises molecular-level qualitative data, such as FT ICR-MS data. If such data exists, the system proceeds to process the data at step 1434. If qualitative data is not available, the system proceeds to process the next data type at 1425.

At 1425, the computer system 50, 60 or processor determines if the assay data comprises traditional assay data. If such data exists, the system proceeds to process the data at step 1435.

At 1430 the computer system 50, 60 or processor begins to transform the identified raw assay data that have been categorized by 1420 into exact, molecular-level qualitative, molecular-level qualitative, and traditional assay data. Compound library described at 1431 are used as an input in the processing of these data types at 1432, 1433, 1434 and 1435, respectively.

At 1431, the computer system 50, 60, or processor 1400 provides compound library, e.g., MC Library. Compound library consists of compounds covering compound classes representative of species that may be present in crude oil or petroleum fraction. The library also contains the physical and chemical property data for the compounds as described in the COMPOUNDS LIBRARY and PROPERTIES ESTIMATION sections. The compound library is loaded into memory for use at 1432, 1433, 1434 and 1435 and other subsequent steps that require this information.

At 1432, using exact (e.g., GC-MS) data, the computer system 50,60 or processor selects pure compounds from the compound library (1431) that matches compounds identified in the exact data. If the exact data is a lump data, a signal group is created to represent the lump.

At 1433, using molecular-level quantitative data (e.g., GC-ToF data), the computer system 50, 60 or processor transforms the data: signal strength, carbon number, and DBE into Aspen distribution.

At 1434, using molecular-level qualitative data (e.g., FT ICR-MS data), the computer system 50, 60 or processor transforms the data: signal strength, formula, carbon number, and DBE into Aspen and gamma or uniform segment distributions.

At 1435, the computer system 50, 60 or processor processes the traditional assay data.

At 1440, the computer system 50, 60 or processor uses the processed data resulting from 1430 and conceptual segment library (described at 1441) to set the compositions, compound class weights, conceptual segment types, and segment distributions.

At 1441, the computer system 50, 60 or processor provides a collection of conceptual segment types, and segment number ranges (conceptual segment library) described in the COMPOUND SELECTION AND UI SEGMENT SELECTION section. The conceptual segment library is loaded into memory and used at 1443, 1444, and 1445.

At 1442, the computer system 50, 60 or processor processes exact data (e.g., GC-MS data) by setting absolute compound composition, if the exact data includes compound identity. If the exact data is a lump data, the absolute composition of the signal group created in 1432 is set.

At 1443, the computer system 50, 60 or processor further processes molecular-level quantitative data (e.g., GC-ToF data) by setting compound class weight, conceptual segment type, and segment distribution.

At 1444, the computer system 50, 60 or processor further processes molecular-level qualitative data (e.g., FT ICR-MS data) by setting the conceptual segment type, segment distribution, and initial values for class weight. For qualitative data, class weight and segment distribution will be determined using an iterative process described at 1456 and 1476.

At 1445, the computer system 50, 60 or processor further processes traditional assay data by setting the conceptual segment type, initial segment distribution, and initial values for class weight.

At 1450, the computer system 50, 60 or processor computes compounds and signal groups compositions from class weight and segment distribution values and/or parameters using the libraries at 1431 and information from 1440 and related steps.

At 1452, the computer system 50, 60 or processor fixes the absolute compound or signal group compositions set by the exact data.

At 1453, the computer system 50, 60 or processor further processes molecular-level quantitative data (e.g., GC-ToF data) by computing signal group composition from the Aspen distribution values and class weights and setting the composition of all the signal groups.

At 1454, the computer system 50, 60 or processor further processes molecular-level qualitative data (e.g., FT ICR-MS data) by computing signal group composition from class weights, Aspen distribution values and/or segment distribution parameters, and setting the relative composition of all the signal groups. For qualitative data, the calculated compositions of signal groups cannot be treated as absolute. Instead, their 'relative' values as suggested by the data are maintained. In addition, class weight and segment distribution parameters will be determined using an iterative process described at 1456 and 1476.

At 1455, the computer system 50, 60 or processor further processes traditional assay data by computing signal group composition from segment distribution parameters and class weights, and setting the relative composition of all the signal groups. Since this type of data does not provide molecular level data, the calculated compositions may be significantly different from reality and will be further adjusted as described in steps at 1456 and 1476.

At 1460, the computer system 50, 60 or processor reconciles results from these four data types into the compositions that represent the crude or petroleum fraction. In this step, compounds are also assigned to signal groups according to the heuristics described in the SIGNAL GROUP, and SIGNAL GROUP AND MOLECULE SELECTIONS USING PROBABILITY DISTRIBUTIONS sections.

At 1470, the signal groups compositions determined at 1460 are used to compute the properties of the sample using physical and chemical properties of the constituent compounds obtained from the library at 1431 and using correlations and methods described in the PROPERTIES ESTIMATION section. Examples of physical properties of the sample that can be estimated include, for example, boiling point, liquid density, liquid viscosity or any combination thereof. Examples of chemical properties that can be estimated include carbon content, hydrogen content, oxygen content, nitrogen content, sulfur content, vanadium content, nickel content, or any combination thereof.

At 1471, the computer system 50, 60 or processor determines the composition of the compounds within signal groups from the structural density index distribution function(s) as described hereinabove.

At 1472, the computer system 50, 60 or processor calculates physical and chemical properties of the sample using physical and chemical properties of the constituent signal groups. Properties of the signal group are in turn calculated from the properties of the constituent compounds of the signal group. Properties of the compounds are obtained from the compound library at 1431 and using correlations and methods described in the PROPERTIES ESTIMATION section.

At 1473, the computer system 50, 60 or processor computes the errors (i.e., residual root-mean-square errors) between estimated physical and chemical properties at 1472 and the corresponding experimental data values.

At 1476, the computer system 50, 60 or processor checks to see if the errors at 1473 are within an acceptable pre-set tolerance. If yes, the system proceeds to 1480. If not, the system proceeds to 1456 to adjust class weight and segment distribution parameters and structural density index distribution parameters and iterate back to 1454 and 1455 and applicable subsequent steps to determine new signal group compositions and compound compositions within segment groups.

At 1456, the computer system 50, 60 or processor uses the errors at 1473 and a non-linear least squares algorithm to determine a new estimate of the class weights, segment distribution parameters, and structural density index distribution parameters which are then used in an iterative process for steps 1454 and 1455 and applicable subsequent steps to determine new signal group compositions and compound compositions within segment groups. This iterative process repeats until convergence is achieved at 1476.

At 1480, the computer system 50, 60 or processor consolidates the formed characterization results and input for display to the end users in tabular and graphical formats.

At 1481, the computer system 50, 60 or processor can display the estimated chemical and physical properties for the selected compounds.

At 1482, the computer system 50, 60 or processor can display the residual root-mean-square errors obtained at 1473.

At 1483, the computer system 50, 60 or processor can display the selected compounds and compositions.

At 1484, the computer system 50, 60 or processor can display the experimental composition data derived from all the input assay data types.

At 1490 the computer system 50, 60 or processor terminates the operation and exits.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A computer-implemented method of characterizing chemical composition of a real-world sample containing crude oil or a petroleum fraction, the method comprising:
   by a processor:
   (i) receiving assay data comprising molecular-level assay data of the sample, or both the molecular-level assay data of the sample and traditional assay data of the sample;
   (ii) setting a) absolute compound compositions based on the molecular-level assay data of the sample, b) first compound classes and class weight(s), first conceptual segment type(s), and first segment distribution based on at least part of the molecular-level assay data, and, if the traditional assay data of the sample is received, setting c) second compound classes and class weight (s), second conceptual segment type(s), and second segment distribution based on at least part of the traditional assay data of the sample;
   (iii) determining a) absolute compound compositions as the set absolute compound compositions, b) first compound composition(s) from first segment distribution values, which represent the first segment distribution and the first class weight(s) set based on at least part of the molecular-level assay data, and if the traditional assay data of the sample is received, determining c) second compound composition(s) from second segment distribution parameters, which represent the second segment distribution and the second class weight(s) set based on the traditional assay data of the sample;

(iv) reconciling a) the absolute compound compositions, b) the first compound composition(s), and/or c) the second compound composition(s), thereby obtaining a reconciled compound composition; and (v) adjusting, when the molecular-level assay data includes qualitative molecular-level assay data, the first class weight(s) and adjusting, when the received assay data includes the traditional assay data, the second class weight(s) and the second segment distribution parameters, until physical and/or chemical properties determined for the reconciled compound composition are consistent with corresponding received assay data, thereby obtaining a refined compound composition, the processor outputting the refined compound composition as a characterization of the chemical composition of the real-world sample containing crude oil or a petroleum fraction.

2. The method of claim 1, wherein the absolute compound compositions are absolute signal group compositions, the first compound composition(s) are first signal group composition(s), the second compound composition(s) are second signal group composition(s), and the compound composition(s) are signal group composition(s).

3. The method of claim 1, wherein the molecular-level assay data comprises gas chromatography-mass spectrometry (GC-MS) data, gas chromatography time-of-flight spectrometry (GC-ToF) data, or Fourier transform ion cyclotron resonance mass spectrometry (FT ICR-MS) data.

4. The method of claim 1, wherein the molecular-level assay data comprises exact data, and the method further comprises (1) selecting pure compounds from a compound library based on the exact data, (2) setting absolute compound compositions, and (3) computing absolute compound compositions.

5. The method of claim 1, wherein the molecular-level assay data comprises quantitative molecular-level assay data, and the method further comprises (1) transforming signal strength data derived from the quantitative molecular-level assay data, quantitative molecular-level assay data derived carbon number, and/or quantitative molecular-level assay data derived double bond equivalent (DBE) into a certain distribution; (2) setting first compound class weight(s), first conceptual segment type(s), and first segment distribution based on a certain distribution determined from the quantitative molecular-level assay data; and (3) computing a compound composition from quantitative molecular-level assay data derived class weight(s), quantitative molecular-level assay data derived segment type(s), and quantitative molecular-level assay data derived segment distribution values, wherein the certain distribution is a distribution representing probability of a segment at discrete integer values of the segment number.

6. The method of claim 1, wherein the molecular-level assay data comprises qualitative molecular-level assay data, and the method further comprises (1) transforming signal strength data derived from the qualitative molecular-level assay data, qualitative molecular-level assay data derived formula, qualitative molecular-level assay data derived carbon number, and/or qualitative molecular-level assay data derived double bond equivalent (DBE) into a certain working distribution, a Gamma distribution, and/or uniform segment distribution; (2) setting first compound class weight(s), first conceptual segment type(s), and first segment distribution based on a qualitative molecular-level assay data derived certain working distribution, Gamma distribution, and/or uniform segment distribution; and (3) computing a compound composition from qualitative molecular-level assay data derived class weight(s), qualitative molecular-level assay data derived segment type(s), and qualitative molecular-level assay data derived segment distribution values and/or parameters, wherein the certain working distribution is a distribution representing probability of a segment at discrete integer values of the segment number.

7. The method of claim 1, wherein the first and/or second compound classes comprise, independently, one or more of a paraffin class, a naphthene class, an aromatic class, an olefin class, a mercaptan class, a thiophene or sulfide class having a single sulfur atom class, a thiophene and sulfide class having two sulfur atoms, a sulfoxide class, a sulfur-oxygen class, a neutral nitrogen having a single pyrrole class, a neutral nitrogen class having two pyrrole nitrogens class, a neutral nitrogen-sulfur class, a neutral nitrogen-oxygen class, a basic nitrogen having a single pyridine class, a basic nitrogen having a pyridine and either another pyridine or a pyrrole class, a basic nitrogen-sulfur class, a basic nitrogen-oxygen class, a phenol class, a paraffinic acid class, an aromatic and naphthenic acid class, a nickel porphyrin class, and a vanadium porphyrin class.

8. The method of claim 7, wherein the conceptual segment types for the paraffin class comprise total carbon number, one-branch methylene, and two-branch methylene.

9. The method of claim 7, wherein the conceptual segment types for the naphthene classes comprise total carbon number, naphthenic side ring, and mole fraction of six-membered rings versus five-membered rings.

10. The method of claim 7, wherein the conceptual segment types for the aromatic class comprise total carbon number, aromatic side ring, and naphthenic side ring.

11. The method of claim 1, wherein at least two of exact assay data, quantitative molecular-level assay data, qualitative molecular-level assay data and traditional assay data are received.

12. The method of claim 1, wherein exact assay data, quantitative molecular-level assay data, qualitative molecular-level assay data and traditional assay data are received.

13. The method of claim 1, the method further comprising estimating physical or chemical properties for the sample as a function of the characterization of the chemical composition of the sample.

14. The method of claim 13, wherein the physical properties of the sample being estimated include one or more of normal boiling point, liquid density, liquid viscosity, Conradson Carbon residue, research octane number, motor octane number, cetane number, and Reid vapor pressure.

15. The method of claim 13, wherein estimating chemical properties of the sample comprises calculating from the chemical formula, chemical structure and chemical compositions, including sulfur content, basic nitrogen content, total nitrogen content, carbon content, hydrogen content, carbon to hydrogen ratio, nickel content, vanadium content, oxygen content, paraffin content, isoparaffin content, olefin content, naphthene content, and aromatic content.

16. The method of claim 1, further comprising assigning a signal group for one or more model compounds from a library of model compounds.

17. The method of claim 16, wherein model compounds from the library of model compounds, which correspond to one signal group, have the same class, the same carbon number and the same double bond equivalent.

18. The method of claim 17, wherein the assay data that is received comprises molecular-level assay data comprising exact data, and, the method further comprises, assigning, on the basis of the exact data, one model compound to a specific signal group.

19. The method of claim 17, wherein the assay data that is received comprises molecular-level assay data comprising exact lump data, and, the method further comprises, assigning, on the basis of the exact lump data, a plurality of model compounds to a signal group, the model compounds having the same class and same carbon number.

20. The method of claim 17, wherein the assay data that is received comprises quantitative molecular-level assay data, and, the method further comprises, assigning, on the basis of the quantitative molecular-level assay data, a plurality of model compounds to a signal group, the model compounds having the same class, same carbon number and same double bond equivalent.

21. The method of claim 17, wherein the assay data that is received comprises qualitative molecular-level assay data, and, the method further comprises, assigning, on the basis of the qualitative molecular-level assay data, a plurality of model compounds to a signal group, the model compounds having the same class, same carbon number and same double bond equivalent when a certain distribution is used to represent at least part of the data, and, the method further comprises, assigning, on the basis of the qualitative molecular-level assay data, a plurality of model compounds to a signal group, the model compounds having the same class, same carbon number, same one-branch methylene number, same two-branch methylene number, same aromatic side ring number, and same naphthenic side ring number when the Gamma distribution or uniform distribution is used to represent at least part of the data, wherein the certain distribution is a distribution representing probability of a segment at discrete integer values of the segment number.

22. The method of claim 17, wherein the assay data that is received comprises the traditional assay data, and, the method further comprises, assigning, on the basis of the traditional assay data, a plurality of model compounds to a signal group, the model compounds having the same class, same carbon number, same one-branch methylene number, same two-branch methylene number, same aromatic side ring number, and same naphthenic side ring number.

23. The method of claim 17, wherein, in assigning one or more model compounds to a signal group, exact data has higher priority than exact lump data, exact lump data has higher priority than quantitative molecular-level assay data, quantitative molecular-level data has higher priority than qualitative molecular-level assay data, and qualitative molecular-level assay data has higher priority than traditional assay data; and wherein, when the assay data of differing priority exists which each would allow assigning a model compound to a signal group, the assay data with highest priority is used to assign the model compound to the signal group.

24. The method of claim 17, wherein the assay data that is received comprises the molecular-level assay data comprising exact data, and, the method further comprises, assigning, on the basis of the exact data, a first model compound to a first signal group.

25. The method of claim 17, wherein the assay data that is received comprises the molecular-level assay data comprising exact lump data, and, the method further comprises, assigning, on the basis of the exact lump data, a plurality of model compounds to a signal group to which model compounds have not been assigned on the basis of exact data, the model compounds being assigned to the signal group having the same class, and same carbon number.

26. The method of claim 17, wherein the assay data that is received comprises quantitative molecular-level assay data, and, the method further comprises, assigning, on the basis of the quantitative molecular-level assay data, a plurality of model compounds to a signal group to which model compounds have not been assigned on the basis of exact data or exact lump data, the model compounds being assigned to the signal group having the same class, same carbon number and same double bond equivalent.

27. The method of claim 17, wherein the assay data that is received comprises qualitative molecular-level assay data, and, the method further comprises, assigning, on the basis of the qualitative molecular-level assay data, a plurality of model compounds to a signal group to which model compounds have not been assigned on the basis of exact data, exact lump data or quantitative molecular-level assay data, the model compounds being assigned to the signal group having the same class, same carbon number and same double bond equivalent when a certain distribution is used to represent at least part of the qualitative molecular-level assay data, and, the method further comprises, assigning, on the basis of the qualitative molecular-level assay data, a plurality of model compounds to a signal group to which model compounds have not been assigned on the basis of exact data, exact lump data, quantitative molecular-level assay data, or at least part of the qualitative molecular-level assay data that uses the certain distribution, the model compounds having the same class, same carbon number, same one-branch methylene number, same two-branch methylene number, same aromatic side ring number, and same naphthenic side ring number, wherein the certain distribution is a distribution representing probability of a segment at discrete integer values of the segment number.

28. The method of claim 17, wherein the assay data that is received comprises the traditional assay data, and, the method further comprises, assigning, on the basis of the traditional assay data, a plurality of model compounds to a signal group to which model compounds have not been assigned on the basis of exact data, exact lump data, quantitative molecular-level assay data or qualitative molecular-level assay data, the model compounds being assigned to the signal group having the same class, same carbon number, same one-branch methylene number, same two-branch methylene number, same aromatic side ring number, and same naphthenic side ring number.

29. The method of claim 1, further comprising calculating compound compositions within a signal group using a probability distribution function that describes the structural density index of constituent compounds within signal groups belonging to a cut of the sample.

30. The method of claim 1, further comprising calculating compound compositions within a signal group using a probability distribution function that describes the structural density index of constituent compounds within all signal groups in the sample.

* * * * *